US010983136B2

(12) United States Patent
Colotta et al.

(10) Patent No.: US 10,983,136 B2
(45) Date of Patent: *Apr. 20, 2021

(54) USE OF 1,25-DIHYDROXYVITAMIN D VALUES IN RATIO WITH PTH AS A PROGNOSTIC BIOMARKER

(71) Applicant: DiaSorin S.p.A., Saluggia (IT)

(72) Inventors: Francesco Colotta, Segrate (IT); Fabrizio Bonelli, Casale Monferrato (IT); Frank Blocki, Hayfield, MN (US); Claudia Zierold, St. Paul, MN (US); Joshua Soldo, Prior Lake, MN (US); Gregory Olson, Lakeland, MN (US); Michael Lutterman, New Brighton, MN (US); John Wall, Woodbury, MN (US); Michael New, Bloomington, MN (US); Hector Floyd Deluca, Deerfield, WI (US)

(73) Assignee: DiaSorin S.p.A., Saluggia (IT)

( * ) Notice: Subject to any disclaimer, the term of this patent is extended or adjusted under 35 U.S.C. 154(b) by 164 days.

This patent is subject to a terminal disclaimer.

(21) Appl. No.: 15/651,517

(22) Filed: Jul. 17, 2017

(65) Prior Publication Data
US 2017/0322230 A1 Nov. 9, 2017

Related U.S. Application Data

(63) Continuation-in-part of application No. PCT/IB2016/050230, filed on Jan. 18, 2016, and a continuation-in-part of application No. 14/763,264, filed as application No. PCT/EP2014/051482 on Jan. 27, 2014, now Pat. No. 10,196,449.

(60) Provisional application No. 62/104,802, filed on Jan. 18, 2015.

(30) Foreign Application Priority Data

Jan. 28, 2013 (EP) ..................................... 13152851

(51) Int. Cl.
| | | |
|---|---|---|
| G01N 33/82 | (2006.01) | |
| G01N 33/50 | (2006.01) | |
| G01N 33/68 | (2006.01) | |
| G01N 33/78 | (2006.01) | |
| G01N 33/74 | (2006.01) | |

(52) U.S. Cl.
CPC ......... *G01N 33/82* (2013.01); *G01N 33/5005* (2013.01); *G01N 33/5091* (2013.01); *G01N 33/6893* (2013.01); *G01N 33/74* (2013.01); *G01N 33/78* (2013.01); *G01N 2333/635* (2013.01); *G01N 2800/347* (2013.01); *G01N 2800/60* (2013.01)

(58) Field of Classification Search
CPC ....... G01N 2333/635; G01N 2800/347; G01N 2800/60; G01N 33/5005; G01N 33/5091; G01N 33/6893; G01N 33/74; G01N 33/78; G01N 33/82
See application file for complete search history.

(56) References Cited

U.S. PATENT DOCUMENTS

| | | | |
|---|---|---|---|
| 4,816,417 A | 3/1989 | DeLuca et al. | |
| 4,840,895 A * | 6/1989 | Self ........................ | C07K 16/42 435/18 |
| 6,516,294 B1 | 2/2003 | Norman | |
| 10,196,449 B2 * | 2/2019 | Soldo ................. | C07K 16/2869 |
| 10,501,548 B2 * | 12/2019 | Soldo ..................... | G01N 33/82 |
| 2012/0064533 A1 | 3/2012 | Lawlor et al. | |
| 2012/0094396 A1 | 4/2012 | Petkovich et al. | |
| 2015/0361178 A1 * | 12/2015 | Soldo ................. | C07K 16/2869 435/7.94 |
| 2017/0267770 A1 * | 9/2017 | Soldo ................. | C07K 16/2869 |
| 2017/0322230 A1 | 11/2017 | Colotta et al. | |

FOREIGN PATENT DOCUMENTS

| | | |
|---|---|---|
| EP | 0177531 | 1/1991 |
| EP | 0583945 | 2/1994 |
| EP | 2759550 | 7/2014 |
| EP | 2759551 | 7/2014 |
| WO | WO 1989/001631 | 2/1989 |
| WO | WO 2008/092917 | 8/2008 |
| WO | WO 2013/043310 | 3/2013 |
| WO | WO 2014/114780 A1 * | 7/2014 |

OTHER PUBLICATIONS

Souberbielle et al., "Assay-Specific Decision Limits for Two New Automated Parathyroid Hormone and 25-Hydroxyvitamin D Assays," Clin. Chem., 2005, vol. 51, No. 2, pp. 395-400.*
Biomedica, Liaison, Test Menu, Jan. 2012, pp. 1-16.*
Anderson, J.L., et al. (2011) "Parathyroid Hormone, Vitamin D, Renal Dysfunction, and Cardiovascular Disease: Dependent or Independent Risk Factors?," Am. Heart J. 162(2):331-339.
Chesney, R.W., et al. (1981) "The Circulating Parathyroid Hormonde (PTH) to Calcitriol (1,25OH₂D) Ratio: A Means of Evaluating Calcitriol Synthesis in Disorders of Calcium Metabolism," Pediatric Res. 15(Supp14):505.
Costagliola, S., et al. (1998) "Genetic Immunization Against the Human Thyrotropin Receptor Causes Thyroiditis and Allows Production of Monoclonal Antibodies Recognizing the Native Receptor," J. Immunol. 160:1458-1465.

(Continued)

Primary Examiner — Galina M. Yakovleva

(74) Attorney, Agent, or Firm — Jeffrey I. Auerbach; AuerbachSchrot LLC

(57) ABSTRACT

The present invention relates to the use of 1,25-dihydroxyvitamin D values in ratio with PTH as a prognostic biomarker. More particularly, the present invention relates to a method for predicting or stratifying the risk of worsening renal function (WRF) in a patient at risk of renal injury or affected by renal injury. Levels of 1,25-dihydroxyvitamin D (1,25 (OH)₂D) are measured in a biological sample and taken together with parathyroid hormone (PTH) levels to provide a ratio indicative of the risk of worsening renal function.

11 Claims, 6 Drawing Sheets

Specification includes a Sequence Listing.

(56) References Cited

OTHER PUBLICATIONS

European Search Report EP 13152851.5 (dated 2013) (7 pages).
Haussler, M.R., et al. (1998) "The Nuclear Vitamin D Receptor: Biological and Molecular Regulatory Properties Revealed," J. Bone Miner. Res. 13(3):325-349.
Holick, M.F. (2007) "Vitamin D Deficiency," New England J. Med. 357:266-281.
Holick, M.F., et al. (2008) "Vitamin D Deficiency: A Worldwide Problem with Health Consequences," Am. J. Clin. Nutr. 87(4):1080S-1086S.
International Search Report PCT/EP2014/051482 (WO 2014/114780) (dated 2014) (5 pages).
International Search Report PCT/IB2016/050230 (WO 2016/113720) (dated 2016) (4 pages).
Jones, G., et al. (1998) "Current Understanding of the Molecular Actions of Vitamin D," Physiol. Ref. 78(4):1193-1231.
Lucas, P.A., et al. (1983) "Ratio of Parathyroid Hormone to 1,25-dihydroxycholecalciferol in Early Renal Failure," Kidney Int. Suppl. 16:S171-S174.
Mangelsdorf, D.J., et al. (1995) "The Nuclear Receptor Superfamily: The Second Decade," Cell 83(6):835-839.
Patel, S., et al. (2011) "Changes in Bone Mineral Parameters, Vitamin D Metabolites, and PTH Measurements with Varying Chronic Kidney Disease Stages," J. Bone Miner. Metab. 29:71-79.
Rochel, N., et al. (2000) "The Crystal Structure of the Nuclear Receptor for Vitamin D Bound to Its Natural Ligand," Mol. Cell 5:173-179.
Rudikoff, S., et al. (1982) "Single Amino Acid Substitution Altering Antigen-Binding Specificity," Proc. Natl. Acad. Sci. USA 79:1979-1983.
Singarapu, K.K., et al. (2011) "Ligand-Specific Structural Changes in the Vitamin D Receptor in Solution," Biochemistry 50(51):11025-11033.
Swami, S., et al. (2001) "A New Enzyme-Linked Immunosorbant Assay for the Measurement of Human Vitamin D Receptor," Bone 28(3):319-326.
Väisánen, S., et al. (1997) "Conformational Studies of Human Vitamin-D Receptor by Antipeptide Antibodies, Partial Proteolytic Digestion and Ligand Binding," Eur. J. Biochem. 248:156-162.
Wang, Y., et al. (2012) "Where is the Vitamin D Receptor?," Arch. Biochem. Biophys. 523:123-133.
Written Opinion of the International Searching Authority PCT/EP2014/051482 (WO 2014/114780) (dated 2014) (6 pages).
Written Opinion of the International Searching Authority PCT/IB2016/050230 (WO 2016/113720) (dated 2016) (6 pages).
Alberts, B. et al. (1983) Molecular Biology of the Cell, Garland Publishing, Inc., New York, pp. 724.
Arai, M.A. et al. (2007) "High-Throughput System for Analyzing Ligand-Induced Cofactor Recruitment by Vitamin D Receptor," Bioconjug. Chem. 18(3):614-20.
Arnaud, J. et al. (1993) "*Affinity Differences for Vitamin D Metabolites Associated With the Genetic Isoforms of the Human Serum Carrier Protein (DBP)*," Hum. Genet. 92(2):183-188.
Declaration of Fabrizio Bonelli in support of EP 2 759 550 B1 (2019) 11 pages.
Lexikon der Biochemie, Specktrum Akademisher Verlag GmbH, Heidelberg (2000), p. 299.
Notice of Opposition Filed Regarding EP 13152851.5 (2018) (19 pages).
P11473 (VDR_Human) (2016) UniProtKB/Swiss-Prot Printout (11 pages).
Rachez, C. et al. (1999) "*Ligand-Dependent Transcription Activation by Nuclear Receptors Requires the DRIP Complex*," Nature 398(6730):824-828.
Response to Notice of Opposition Filed Regarding EP 13152851.5 (2018) (23 pages).
Response to Third Party Observations Filed Regarding EP 13152851.5 (2017) (5 pages).
Scheefers-Borchel, U. et al. (1985) "*Discrimination Between Fibrin and Fibrinogen by a Monoclonal Antibody Against a Synthetic Peptide*," Proc. Natl. Acad. Sci. (U.S.A.) 82:7091-7095.
Self, C.H. et al. (2013) "*Non-Competitive Immunoassays for Small Molecules—The Anti-Complex and Selective Antibody Systems*," In: The Immunoassay Handbook, pp. 61-65.
Smit et al. (2005) "*Comparison of Four Different Assays for Determination of Serum S-100B*," Int. J. Biol. Markers 20(1):34-42.
Staal, A. et al. (1996) "*Distinct Conformations of Vitamin D Receptor/Retinoid X Receptor Alpha Heterodimers Are Specified by Dinucleotide Differences in the Vitamin D-Responsive Elements of the Osteocalcin and Osteopontin Genes*," Molec. Endocrinol. 10(11):1444-1456.
Strathmann, F.G. et al. (2011) "Quantification of 1α,25-Dihydroxy Vitamn D by Immunoextraction and Liquid Chromatography—Tandem Mass Spectrometry," Clin. Chem. 57(9):1279-1285.
Third Party Observations Filed Regarding EP 13152851.5 (2017) (6 pages).
Van Belden, J. et al. (2014) "Experience with the First Fully Automated Chemiluminescence ImmunoAssay for the Quantification of 1α,25-dihydroxy-vitamin D," Clin. Chem. Lab. Med. 53(5):761-770.
Yang, W. et al. (1999) "*20-Epi Analogues of 1,25-Dihydroxyvitamin D3 Are Highly Potent Inducers of DRIP Coactivator Complex Binding to the Vitamin D3 Receptor*," J. Biol. Chem. 274(24):16838-16845.

* cited by examiner

USE OF 1,25-DIHYDROXYVITAMIN D VALUES IN RATIO WITH PTH AS A PROGNOSTIC BIOMARKER

CROSS-REFERENCE TO RELATED APPLICATIONS

This application is a continuation-in-part of U.S. Patent Appln. Serial No. PCT/IB2016/050230 (filed on Jan. 18, 2016; now expired), which claims priority to U.S. Patent Appln. Ser. No. 62/104,802 (filed on Jan. 18, 2015; now expired); this application is also a continuation-in-part of U.S. patent application Ser. No. 15/606,284 (filed on May 26, 2017; issued Dec. 10, 2019 as U.S. Pat. No. 10,501,548), which application is a division of U.S. patent application Ser. No. 14/763,264 (filed on Jul. 24, 2015; issued Feb. 5, 2019 as U.S. Pat. No. 10,196,449), which application is a § 371 application of PCT/EP2014/051482 (filed on Jan. 24, 2014; now lapsed), which claims priority to European Patent Application EP 13152851.5 (filed on Jan. 28, 2013); each of these patent applications is hereby incorporated by reference in its entirety.

REFERENCE TO SEQUENCE LISTING

This application includes one or more Sequence Listings pursuant to 37 C.F.R. 1.821 et seq., which are disclosed in computer-readable media and were filed (file name: 0400_0007C_ST25_1.txt, created on Jul. 14, 2017, and having a size of 4,356 bytes), which file is herein incorporated by reference in its entirety.

FIELD OF THE INVENTION

The present invention relates to a method for predicting or stratifying the risk of worsening renal function (WRF) in a patient at risk of renal injury or in a patient affected by renal injury. Levels of 1,25-dihydroxyvitamin D (1,25(OH)$_2$D) are measured in a biological sample and taken together with parathyroid hormone (PTH) levels to provide a ratio indicative of the risk of worsening renal function.

BACKGROUND OF THE INVENTION

Progressive deterioration of renal function is common in patients with different diseases such as chronic heart failure (HF), chronic kidney disease (CKD) and metabolic syndrome, and is associated with unfavorable outcomes, which can be improved by timely interventions.

The cross talk between the diseased heart and kidney is a growing burden for health care systems as the incidence of HF and chronic kidney disease (CKD) has been steadily increasing and will further increase due to ageing of the general population and better treatment of acute cardiac and renal diseases. It has also been realized that the progressive development of worsening renal function (WRF) over time carries an increased risk of death and hospitalizations.

Identifying patients at risk of worsening renal function (WRF) is important for their clinical management, and might lead to less frequent hospitalizations and to the prevention of adverse outcomes. Early prediction and identification of patients at risk for future WRF may also be useful to optimize therapies and to improve outcomes. Circulating biomarkers may therefore provide a simple and objective means to predict deterioration in renal function in patients with chronic HF or other diseases such as chronic kidney disease (CKD) or IgA nephropathy. For instance, a common marker of renal injury is serum creatinine, which however is slowly affected by changes in renal function and is also dependent on a plurality of different factors such as muscle mass, sex, race and age.

Disturbances of mineral metabolism, and in particular to the parathyroid hormone (PTH)/vitamin D axis, are characteristic of decreased renal function (Evenepoel, P. et al. (2014) "Laboratory Abnormalities in CKD-MBD: Markers, Predictors, or Mediators of Disease?" Semin. Nephrol. 34(2):151-163). Recent studies indicate that vitamin D-deficiency may promote or accelerate the progression of CKD. Cross-sectional studies have shown higher circulating levels of PTH and lower levels of vitamin D metabolites as CKD progresses (lower estimated glomerular filtration rate, eGFR). To the inventors' knowledge, there are, however, scant reports on the ability of circulating markers of bone mineral metabolism to predict deterioration of renal function over time.

Therefore, the inventors examined the relation between two markers of the vitamin D/PTH axis and worsening of renal function (WRF) in a large cohort of patients with HF.

Lack of reliable automated testing of 1,25-dihydroxyvitamin D (1,25(OH)$_2$D), the biologically active metabolite of vitamin D, has in the past precluded evaluation of the prognostic value of this measurement.

Therefore, there is a need to identify biomarkers for predicting or stratifying the risk of worsening renal function (WRF) in a patient at risk of renal injury or in a patient affected by renal injury.

SUMMARY OF THE INVENTION

The present invention provides a method for predicting or stratifying the risk of worsening renal function (WRF) in a patient at risk of renal injury or in a patient affected by renal injury, using the level of 1,25(OH)$_2$D in conjunction with the level of parathyroid hormone (PTH) to determine the ratio of 1,25(OH)$_2$D to PTH. The ratio value allows for risk prediction or stratification of worsening renal function in the patient.

The term "PTH" as used in the present description preferably refers to parathyroid hormone 1-84 (PTH 1-84), which is the biologically active hormone produced by the parathyroid glands and secreted into the systemic circulation.

Therefore, the invention provides a method for predicting or stratifying the risk of worsening renal function (WRF) in a patient at risk of renal injury or in a patient affected by renal injury, the method comprising: (a) detecting and quantifying 1,25(OH)$_2$D in a sample from the patient; (b) detecting and quantifying PTH in a sample from the patient; and (c) calculating the 1,25(OH)$_2$D to PTH ratio, wherein when the ratio is above a predetermined threshold, the patient is predicted or stratified not to have an increased risk of worsening renal function, and when the ratio is below a predetermined threshold, the patient is predicted or stratified to have an increased risk of worsening renal function.

The measurement of the ratio of 1,25(OH)$_2$D to PTH in patients at risk of renal injury or in patients affected by renal injury offers several advantages, such as improvement of the area under the receiver operating curve, translating added clinical value, integration of more than one physiopathologicaly interrelated biomarker and modulation of two different hormones to increase the significance of the ratio.

In various embodiments, 1,25(OH)$_2$D and/or PTH are determined from blood, plasma or serum samples from the patient. In these and other embodiments, 1,25(OH)$_2$D and/or PTH are determined using an immunoassay. In particular embodiments, the immunoassay is a chemiluminescent assay.

In one embodiment, when the ratio of 1,25(OH)$_2$D to PTH is below the predetermined threshold, the patient is predicted or stratified as having a high risk of worsening of renal function.

In another embodiment, when the 1,25(OH)$_2$D to PTH ratio is above the predetermined threshold, the patient is predicted or stratified as having a low risk of worsening renal function.

The present invention is particularly directed to a method for predicting or stratifying the risk of worsening renal function (WRF) in a patient at risk of renal injury or affected by renal injury, the method comprising:
(a) incubating a sample of serum or plasma or blood from the patient in a reaction container in the presence of a receptor protein comprising the Ligand Binding Domain of Vitamin D Receptor (VDR-LBD), and a capture moiety that specifically binds to a conformational epitope of VDR-LBD when the VDR-LBD is complexed with 1,25-dihydroxyvitamin D;
  wherein the complexing of VDR-LBD and 1,25-dihydroxyvitamin D does not naturally occur in serum, plasma or blood, and the capture moiety does not specifically bind to VDR-LBD or to 1,25-dihydroxyvitamin D that are not complexed with one another; and
  wherein the incubation is under conditions sufficient to permit the determination of the concentration of 1,25-dihydroxyvitamin D in the serum, plasma or blood; and
(b) assaying the concentration of parathyroid hormone (PTH) in the serum, plasma or blood;
wherein:
when the [1,25-dihydroxyvitamin D]/[parathyroid hormone] ratio is above a predetermined threshold, the patient is predicted or stratified not to have an increased risk of worsening renal function, and
when the [1,25-dihydroxyvitamin D]/[parathyroid hormone] ratio is below a predetermined threshold, the patient is predicted or stratified to have an increased risk of worsening renal function.

Preferably, the predetermined threshold in these embodiments is comprised within the range of from 0.92 to 1.8, more preferably the predetermined threshold is 0.92, 0.98 or 1.68.

In yet another embodiment, 1,25(OH)$_2$D is determined using an immunoassay which comprises (i) contacting the 1,25(OH)$_2$D in the sample from the patient with a receptor protein comprising the Ligand Binding Domain of Vitamin D Receptor (VDR-LBD), thereby obtaining a first complex; (ii) contacting the first complex with a capture moiety that specifically binds to a conformational epitope on the first complex, but does not bind to either 1,25(OH)$_2$D or VDR-LBD that is not bound in the first complex, thereby obtaining a second complex; and (iii) detecting and quantifying the second complex as an indication of the amount of 1,25 (OH)$_2$D in the sample.

The invention particularly includes a method wherein 1,25-dihydroxyvitamin D is detected and quantified using an immunoassay which comprises:
(i) contacting 1,25-dihydroxyvitamin D in the sample with a receptor protein comprising the Ligand Binding Domain of Vitamin D Receptor (VDR-LBD), thereby obtaining a first complex;
(ii) contacting the first complex with a capture moiety that specifically binds to a conformational epitope on the first complex, thereby obtaining a second complex; wherein the capture moiety does not specifically bind to either 1,25-dihydroxyvitamin D or VDR-LBD that is not bound in the first complex; and
(iii) detecting and quantifying the second complex as an indication of the amount of 1,25-dihydroxyvitamin D in the sample.

In a preferred embodiment, the capture moiety is a monoclonal antibody.

Preferably, the capture moiety is immobilized on or to a solid support.

In another preferred embodiment, the immunoassay of the claimed method is a sandwich immunoassay.

In a more preferred embodiment, step (iii) of detecting and quantifying the second complex is carried out by means of a labeled anti-VDR-LBD detector antibody.

Further, while the present 1,25(OH)$_2$D data was obtained using a new immunoassay that provides rapid, sensitive and reproducible data using significantly smaller volumes of samples than other available assays, those skilled in the art will appreciate that any method of collecting reliable (sufficiently sensitive and accurate) values for 1,25(OH)$_2$D and PTH is contemplated. For example, such methods may include GC-MS, LC-MS/MS and the like.

The invention also provides a kit, being an article of manufacture, that comprises:
(A) a first container that contains Ligand Binding Domain of Vitamin D Receptor (VDR-LBD) and an antibody, or epitope-binding fragment thereof, that specifically binds to a conformational epitope of VDR-LBD when the VDR-LBD is complexed with 1,25-dihydroxyvitamin D in serum or plasma or blood, and does not specifically bind to VDR-LBD or to 1,25-dihydroxyvitamin D that are not complexed with one another; and
(B) a second container that contains a detectably-labelled reagent capable of binding to parathyroid hormone (PTH).

The invention particularly pertains to the embodiment of such a kit wherein the antibody, or epitope-binding fragment thereof, that specifically binds to the conformational epitope of VDR-LBD is immobilized to a solid support (and especially a magnetic bead) in the first container.

The invention also pertains to the embodiment of such kits wherein the antibody that specifically binds to the conformational epitope of VDR-LBD is a monoclonal antibody.

The invention particularly pertains to the embodiment of such kits wherein the kit is a Reagent Integral that is a multi-chambered cartridge specially adapted for use in an automated analyzing device, wherein the first and second containers of the kit are chambers of the Reagent Integral.

These and other features and advantages of the present invention will be set forth or will become more fully apparent in the description that follows and in the appended claims. The features and advantages may be realized and obtained e.g. by means of the instruments and combinations particularly pointed out in the appended claims. Furthermore, the features and advantages of the invention may be learned by the practice of the invention or will be apparent from the description, as set forth hereinafter.

BRIEF DESCRIPTION OF THE FIGURES

Various exemplary embodiments of the compositions and methods according to the invention will be described in detail, with reference to the following figures wherein.

DETAILED DESCRIPTION OF THE EXEMPLARY EMBODIMENTS

Figure 1:
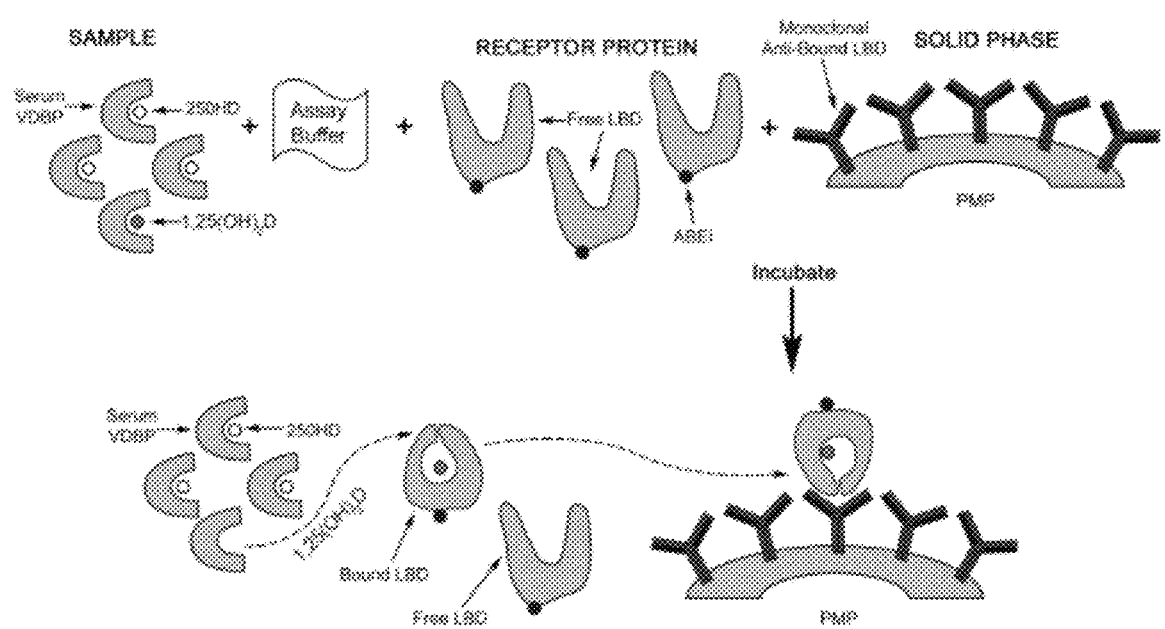
FIG. 1 Illustrates one-site, non-competitive immunoassays according to the invention, wherein the complex formed via the binding of 1,25(OH)$_2$D to the labeled receptor protein which comprises the Ligand Binding Domain of Vitamin D Receptor (VDR-LBD) is captured by the conformation-specific capture antibody of the invention (designated as "Monoclonal Anti-Bound LBD") immobilized on or to a solid support (a paramagnetic particle (PMP)) and the label is Amino-Butyl-Ethyl-Isoluminol (ABEI). The step of adjusting the pH of the biological fluid sample with the assay buffer and the step of adding the receptor protein comprising the VDR-LBD to the sample, are performed simultaneously.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Abbreviations used throughout this text are as follows: HF, Heart Failure; NYHA, New York Heart Association; PPV, Positive Predictive Value; NPV, Negative Predictive Value; LVEF, left ventricular ejection fraction; GFR, glomerular filtration rate; eGFR, estimated glomerular filtration rate; CV, cardiovascular; 1,25(OH)$_2$D, 1,25-dihydroxyvitamin D; PTH, parathyroid hormone; ROC, receiver operating characteristics; AUC, area under the curve; CART, Classification and regression trees.

The term "antibody" as used in the present description encompasses a whole antibody molecule (including polyclonal, monoclonal, chimeric, humanized, or human versions having full length heavy and light chains) as well as an antigen binding antibody fragment. An "antibody fragment" includes any immunoglobulin fragment having the same binding specificity as the corresponding whole antibody. Such fragments are produced according to standard methods; cf. for example Harlow and Lane, "Antibodies, A Laboratory Manual", CSH Press, Cold Spring Harbor, USA, 1988. Non-limiting examples of antibody fragments include F(ab), Fab', F(ab')$_7$, F(v), single chain antibodies (scFv), F(c), F(d).

The term "vitamin D" as used in the present description refers both to vitamin D$_3$ (cholecalciferol) and vitamin D$_2$ (ergocalciferol), and the term "1,25(OH)$_2$D" refers to both 1,25(OH)D$_3$ and 1,25(OH)D$_2$. Analogues of 1,25(OH)$_2$D include modified versions and structural analogues thereof, such as for example, 19-nor-1α-25-dihydroxyvitamin D$_2$ (e.g. Zemplar or paricalcitol from Abbott), 1α-hydroxyvitamin D$_2$ or 1α-hydroxyergocalciferol (e.g. Hectorol or doxercalciferol from Genzyme), and 2-methylene-19-nor-(20S)-1α,25-(OH)$_2$D$_3$ (e.g. 2MD from Deltanoid Pharmaceuticals).

Vitamin D is a steroid hormone which plays a fundamental role in skeletal metabolism and calcium homeostasis. In humans and animals, the major forms of vitamin D are vitamin D$_3$ (cholecalciferol) and vitamin D$_2$ (ergocalciferol). Vitamin D$_3$ is primarily synthesized in the skin from 7-dehydrocholesterol in response to exposure to solar ultraviolet-B (UVB), but vitamin intake can also occur from dietary sources such as oily fish, i.e. salmon and mackerel. Vitamin D$_2$ is primarily acquired in the diet from fungal and vegetable sources as well as from supplementation (e.g. Drisdol™ or Sterogyl 15 "A").

Irrespective of the source, the conversion of vitamins D$_2$ and D$_3$ into a bioactive compound requires two separate hydroxylation steps. In the liver, the enzyme 25-hydroxylase converts vitamin D to 25-hydroxyvitamin D (hereinafter designated as "25(OH)D"). This intermediary metabolite is the major circulating form of the hormone and serves as a reservoir for further hydroxylation to the biologically active metabolite 1,25-dihydroxyvitamin D (hereinafter designated as "1,25(OH)$_2$D").

The latter step takes place primarily in the renal tubular cells and is catalyzed by the enzyme 1-alpha-hydroxylase. The plasma concentrations of 1,25(OH)$_2$D are highly regulated by a variety of factors, including the serum parathyroid hormone (PTH), and they are normally about 1000-fold lower than the precursor compound 25(OH)D.

Because of their lipophilic nature, the majority of vitamin D and metabolites thereof circulate in the blood-stream bound to the vitamin D binding protein (DBP) (80-90%), also known as Gc-Globulin, and albumin (10-20%). DBP has high affinity for vitamin D metabolites (Ka=5×10$^8$M$^{-1}$ for 25(OH)D and 24,25(OH)$_2$D, 4×10$^7$M$^{-1}$ for 1,25(OH)$_2$D and vitamin D), such that under normal circumstances only approximately 0.03% 25(OH)D and 24,25(OH)$_2$D and approximately 0.4% 1,25(OH)$_2$D are in a free form.

The biological effects of 1,25(OH)$_2$D are mediated primarily by the binding of this bioactive hormone to a specific intracellular Vitamin D Receptor (VDR), which acts primarily by regulating the expression of genes whose promoters contain specific DNA sequences known as Vitamin D Response Elements (VDREs).

The Vitamin D Receptor (VDR) is a ligand-dependent transcriptional regulator belonging to the superfamily of nuclear receptors (NRs). Like the other members of this receptor family, the VDR possesses a modular structure which comprises an amino-terminal A/B domain, a highly conserved DNA-Binding Domain (DBD), a flexible linker region and a C-terminal Ligand-Binding Domain (LBD) which is more variable (Mangelsdorf D J et al., 1995, *Cell* 83(6):835-9). The C-terminal LBD is a globular multifunctional domain, responsible for hormone binding, dimerization with Retinoid X Receptor (RXR) and interaction with co-repressors and co-activators, which all together are critical for the regulation of transcriptional activities (Haussler M R, et al. 1998, *J Bone Miner Res.* 13(3):325-49).

The Ligand Binding Domain (LBD) of VDR has been crystallized and its structure solved (Rochel N, Wurtz J M, Mitschler A, Klaholz B, Moras D., "*The Crystal Structure Of The Nuclear Receptor For Vitamin D Bound To Its Natural Ligand,*" Mol Cell 2000; 5:173-179).

The binding of the ligand to the VDR induces a conformational change at the Ligand Binding Domain of the receptor, which in turn increases heterodimerization of VDR with a cofactor, the Retinoid X Receptor (RXR), on a Vitamin D-Responsive Element (VDRE) in the promoter region of the target genes. This in turn leads to opening of the promoter to the transcriptional machinery (Glenville J. et al., 1998 *Physiological Reviews* 78(4):1193-1231).

Nuclear receptor Ligand Binding Domains (LBDs) are known to have a high content of alpha-helix, which may undergo a large conformational change in response to ligand binding, forming up a hydrophobic pocket. Recently, differences in the conformation of the *Rattus norvegicus* Ligand-Binding Domain (r-VDR-LBD) when bound to diverse ligands were solved by NMR spectroscopy (Kiran K. Singarapu et al. 2011 *Biochemistry* 50 (51): 11015-24).

Vitamin D is currently recognized as a pro-hormone which has multiple roles in maintaining optimal health in human beings. It has long been established that marked vitamin D deficiency results in histologically evident bone diseases such as osteomalacia in adults and rickets in children, while vitamin D insufficiency may cause alterations in the parathyroid hormone concentration which, if persisting over time, may contribute to bone loss and fracture. However, although initially identified as a classic regulator of calcium homeostasis, vitamin D is now known to have a broader spectrum of actions, driven by the wide expression and distribution in human tissues of the vitamin D receptor (VDR).

In the last decades, clinical and epidemiological data have provided several evidences that impaired levels of 25(OH)D are associated with an increasing risk of various chronic diseases including cardiovascular diseases, hypertension, myocardial infarction, diabetes, cancer, reduced neuromuscular function, infectious and autoimmune diseases. Even complications of pregnancy such as pre-eclampsia, gestational diabetes, cesarean section, and premature birth might be the tragic sequela of gestational vitamin D deficiencies (Holick M F; 2007 *N Engl J Med.* 357(3):266-81, Holick M F and Chen T C. 2008 *Am J Clin Nutr.*; 87(4):1080S-6S).

Impaired levels of 25-Hydroxyvitamin D (25(OH)D) (calcidiol) have previously been shown to be associated with an increased risk of various diseases including cardiovascular disease, hypertension, myocardial infarction, diabetes, cancer, reduced neuromuscular function, infectious and autoimmune disease. However, under conditions of vitamin D (cholecalciferol) deficiency, this biomarker may not be as predictive as its biologically active metabolite 1,25-dihydroxyvitamin D (1,25(OH)$_2$D) or calcitriol. 1,25(OH)$_2$D and PTH control calcium and phosphate homeostasis. The potential value of 1,25(OH)$_2$D testing as a significant predictor of renal injury or of worsening renal function in a cohort of patients, more particularly HF patients, was pursued in a patient model population.

However, very few studies have been carried out to associate risks of chronic disease to 1,25(OH)$_2$D levels, due to both complexity and lack of reliability of the measurement methods which are available today.

Therefore, the determination of circulating 1,25(OH)$_2$D, which is the active form of vitamin D, is becoming of increasing relevance in many different clinical applications, either as a diagnostic marker and/or as a therapy monitoring indicator. For instance, the determination of serum 1,25(OH)$_2$D and parathyroid hormone (PTH) levels and a possible correlation thereof may represent an important measure for aiding in the diagnosis of parathyroid diseases as well as for the detection of the onset of secondary hyperparathyroidism in the course of renal failure or the development of vitamin D-resistant rickets (VDRR).

Currently, both in routine clinical and research use there is a wide range of methodologies available for measuring the circulating levels of total 25(OH)D (i.e., 25(OH)D$_3$+25(OH)D$_2$). Commercial, fast, automated chemiluminescence-based immunoassay methods are supplied by Abbott Diagnostics (Abbott Park, Ill., USA, ARCHITECT 25-OH vitamin D assay), DiaSorin Inc. (Stillwater, Minn., USA, LIAISON® 25 OH Vitamin D Total Assay), Immunodiagnostic Systems (Boldon, England, IDS-iSYS 25-Hydroxy Vitamin D (25OHD)), Roche Diagnostics (Mannheim, Germany, Modular Analytics E170 Elecsys® Vitamin D Total assay), and Siemens Healthcare Diagnostics (Tarrytown, N.Y., USA, ADVIA Centaur® Vitamin D Total assay). Besides these assay platforms, there has recently been a steady increase in the use of physical methods based on chromatographic separation followed by non-immunological direct detection (semi-automated liquid chromatography-tandem mass spectrometry, LC-MS/MS), which have been principally developed in specialist laboratories in the United States (e.g. Esoterix Inc. in Calabasas Hills, Calif., Mayo Clinic in Rochester, Minn., ARUP Laboratories in Salt Lake City, Utah and Quest Diagnostics in Lyndhurst, N.J.), Europe (e.g. Ghent University in Ghent, Belgium, and CHU de Liége in Liége, Belgium) and Australia (e.g. Pathology Queensland in Herston Queensland, and Douglass Hanly Moir Pathology in Macquarie Park NSW).

Despite the wide selection of assay platforms for measuring 25(OH)D, there are no automated assay methods currently available for the quantitative determination of the active form of vitamin D in clinical samples. The systemic circulating levels of 1,25(OH)$_2$D are extremely low, in the pg/ml range, and therefore represent a significant bioanalytical challenge for clinical monitoring. Quantitation of 1,25(OH)$_2$D in plasma has been traditionally carried-out by radioimmunoassay (MA). In order to avoid problems related to handling of radioactivity and the limited shelf-life of radioactive labels, new vitamin D testing methods have recently emerged which mainly rely upon the employment of the LC-MS/MS methodology. However, the reported LC-MS/MS bioanalytical assays for 1,25(OH)$_2$D suffer from the extensive sample preparation procedures or derivatization protocols which need to be carried out in order to achieve the requisite sensitivity and selectivity. At present, the main methods available for the detection of 1,25(OH)$_2$D require performing a number of sample pre-treatment or pre-analytical steps which are usually carried-out manually and may therefore be very time consuming, labor-intensive, and expensive.

EP 0 583 945 A discloses an assay for 1,25(OH)$_2$D which involves extracting blood serum using an organic solvent such as ethyl acetate, separating out potentially interfering other vitamin D metabolites using a silica column, and then adding pig receptor protein, radiolabeled 1,25(OH)$_2$D, biotinylated antibody capable of binding to the receptor, and a facilitator protein such as BSA as part of an immunoprecipitation competitive binding assay.

WO 89/01631 discloses a competitive binding assay for 1,25(OH)$_2$D which involves adding pig receptor protein, radiolabeled 1,25(OH)$_2$D and biotinylated antibody capable of binding to the receptor to untreated blood serum. The competitive binding assay requires the use of vitamin D transport protein which acts as a screen to minimize interference from related metabolites.

Swami, S. et al., Bone, Vol. 28, No. 3, March 2001:319-326 discloses an antibody which binds to the hinge portion of the vitamin D receptor (VDR) and which is used in a method for the measurement of VDR. However, such antibody is not able to distinguish between ligand-occupied and -unoccupied VDR and is therefore not useful for the detection of 1,25(OH)$_2$D.

The DiaSorin RIA (Part No. 65100E/100 Tubes; 1,25-Dihydroxyvitamin D) involves the use of organic solvents, extraction instrumentation, and C18-OH columns to separate out potentially interfering vitamin D metabolites such as 24,25(OH)$_2$D, 25,26(OH)$_2$D and 25(OH)D in order to isolate 1,25(OH)$_2$D from the test sample prior to metabolite measurement.

Even the recently commercialized automated assay supplied by Immunodiagnostics for the determination of 1,25 (OH)$_2$D (Part No. IS-2400; IDS-iSYS 1,25-Dihydroxyvitamin D) requires a time-consuming and labor-intensive sample pre-treatment step which makes use of the IDS proprietary Immunocapsules.

Furthermore, the prior art methods often suffer from limitations in term of assay specificity since cross-reactivity events with other vitamin D metabolites not completely removed from the test specimens during the pre-analytical or sample pre-treatment steps may lead to the measurement of erroneous higher concentrations of 1,25(OH)$_2$D. For example, most immunoassay antibodies significantly cross-react with 25(OH)D, 24,25(OH)$_2$D, and 25,26(OH)$_2$D which may be present in blood at levels 1000-fold greater than 1,25(OH)$_2$D.

There is therefore a strong need to develop an assay method for detecting total 1,25(OH)$_2$D (1,25(OH)$_2$D$_2$+1,25 (OH)$_2$D$_3$) which does not suffer from the drawbacks and limitations of the prior art.

In particular, there is a need for an assay method which would enable precise, sensitive and accurate detection of total 1,25(OH)$_2$D (1,25(OH)$_2$D$_2$+1,25(OH)$_2$D$_3$) without requiring time-consuming and labor-intensive sample pre-treatment steps and which may possibly be provided in an automated format.

There is also a need for a 1,25(OH)$_2$D assay method which substantially does not cross-react with other vitamin D metabolites which may be present in the test sample.

These and other needs are met by the method, and the related kit and antibodies, disclosed in PCT Patent Publication WO 2014/114780 and in US Patent Publication No. 2015-0361178, which form an integral part of the present description.

In particular, PCT Patent Publication WO 2014/114780 and US Patent Publication No. 2015-0361178 disclose the finding that the pH of the medium in which the assay is performed significantly influence the binding affinity of vitamin D binding protein (DBP) and of the Ligand Binding Domain of Vitamin D Receptor (VDR-LBD) to 1,25 (OH)$_2$D.

The results of experiments presented in PCT Patent Publication WO 2014/114780 and in US Patent Publication No. 2015-0361178 clearly showed that a shift in the pH value of the test sample above 6, preferably above 7, surprisingly induces an increase of about 200-fold in the affinity of VDR-LBD for 1,25(OH)$_2$D over 25(OH)D, while at the same pH value DBP exhibits about 1000-fold greater affinity for 25(OH)D over 1,25(OH)$_2$D. The exploitation of such an advantageous effect of the pH on the equilibrium between 1,25(OH)$_2$D bound to DBP and 1,25(OH)$_2$D bound to VDR-LBD represents therefore a unique tool in terms of both ease and effectiveness for selectively capturing circulating 1,25(OH)$_2$D from natural DBP in the presence of a molar excess of VDR-LBD, while leaving at the same time the majority of 25(OH)D in a sequestered form bound to DBP. Such an approach is particularly advantageous over the prior art methods, which require time-consuming and labor-intensive sample pre-treatment steps to allow the determination of 1,25(OH)$_2$D in clinical samples.

Since the binding of 1,25(OH)$_2$D to VDR-LBD is known to induce a conformational change in the VDR-LBD molecule, the present inventors have conducted extensive experimentation to develop a capture moiety, such as an antibody, capable of specifically recognizing and binding to VDR-LBD bound to 1,25(OH)$_2$D without cross-reacting with uncomplexed VDR-LBD, in order to selectively discriminate the VDR-LBD/1,25(OH)$_2$D complex from unbound VDR-LBD in various biological matrices. Such conformation-specific capture moiety is particularly useful, since it represents an invaluable tool for the rapid and reliable detection of the circulating active form of vitamin D.

As mentioned above, a characterizing feature of the detection method disclosed in PCT Patent Publication WO 2014/114780 and in US Patent Publication No. 2015-0361178 is that the pH of the biological fluid sample under examination is adjusted to a value above 6, i.e. comprised between 6 and 9. Preferred pH values are comprised between 7 and 8.6, such as 7.2, 7.3, 7.4, 7.5, 7.6, 7.7, 7.8, 7.9, 8.0, 8.1, 8.2, 8.3, 8.4, 8.5 or 8.6. Buffering agents and buffer solutions suitable for adjusting the pH of a biological fluid sample to the above-mentioned values are well known to those skilled in the art.

In the context of the present invention, the biological fluid sample is preferably selected from the group consisting of whole blood, serum, plasma, and urine. The biological fluid sample may optionally include further components, such as for example: diluents, preservatives, stabilizing agents and/or buffers. If needed, dilutions of the biological fluid sample are prepared using any suitable diluent buffer known in the art.

The detection method disclosed in PCT Patent Publication WO 2014/114780 and in US Patent Publication No. 2015-

0361178 is further characterized in that a receptor protein comprising the Ligand Binding Domain of Vitamin D Receptor (VDR-LBD) is employed in order to bind 1,25 (OH)$_2$D or analog thereof.

The term "receptor protein comprising the Ligand Binding Domain of Vitamin D Receptor (VDR-LBD)" as used in the present description encompasses both the whole Vitamin D Receptor protein (VDR), which includes the C-terminal Ligand Binding Domain, and the Ligand Binding Domain (LBD) of Vitamin D Receptor in an isolated or engineered form.

For example, the whole Vitamin D Receptor protein or the Ligand Binding Domain thereof is a recombinant protein generated by DNA technologies. Nucleotide sequences encoding Vitamin D Receptor from various animal species are available and characterized. Thus, the whole Vitamin D Receptor protein or the Ligand Binding Domain thereof used in PCT Patent Publication WO 2014/114780 and in US Patent Publication No. 2015-0361178 as the receptor protein is, for example but without limitation, of mammalian origin (e.g., a human, mouse or rat protein), or of avian origin, or of amphibian origin; alternatively, it is a mutated variant of any of such proteins.

Optionally, the whole Vitamin D Receptor protein or the Ligand Binding Domain thereof used as the receptor protein in the present invention further comprises or is coupled to an affinity tag, in order to substantially improve purification and/or detection procedures. Among the most common affinity tags, polyhistidine tags ("His-tag") attached at the C-terminal or N-terminal of the protein of interest are routinely employed in protein sciences and their use within the context of the present invention is therefore well within the knowledge of the person skilled in the art. Expressed His-tagged proteins are easily purified e.g. on matrices containing transitional metal ions, and the use of anti-His-tag antibodies represents a useful and known tool in localization and immunoprecipitation studies.

In order to produce recombinant VDR-LBD proteins to be used as suitable reagents for the methods and kits of the invention, the plasmid-based expression vector described in PCT Patent Publication WO 2014/114780 and in US Patent Publication No. 2015-0361178 is preferably employed. Briefly, DNA coding for the ligand binding domain of the vitamin D receptor from *Rattus norvegicus* residues 116-423 with deletion of a 47 amino acid internal loop (165-211) (rVDR-LBD) was cloned into the pET-29b plasmid (Novagen) by using the Nde I/Bgl II restriction site combination. To facilitate the detection and purification of recombinant VDR-LBD protein, a polyhistidine tag can be added at the C-terminus of the protein of interest by cloning a His tag coding sequence downstream of the VDR-LBD coding sequence, followed by a stop codon.

Therefore, in a preferred embodiment of the method disclosed in PCT Patent Publication WO 2014/114780 and in US Patent Publication No. 2015-0361178 the whole Vitamin D Receptor protein or the Ligand Binding Domain thereof used as the receptor protein is a recombinant His-tagged fusion protein. However, other affinity tags such as, for example, Arg5, Strep-tag II, FLAG, fluorescein (FITC), Poly(A), Poly(dT) and biotin may be employed. Techniques for the production of epitope-tagged recombinant proteins are generally known in the art. In another preferred embodiment, the whole Vitamin D Receptor protein or the Ligand Binding Domain thereof used as the receptor protein is coupled to a chaperone protein or in general to any other protein which has a chaperone-like function, in order to help protein folding and/or improve stability. A receptor protein (i.e. the whole Vitamin D Receptor protein or the Ligand Binding Domain thereof, possibly coupled to an affinity tag or a chaperone or chaperone-like protein) bearing an amino acid sequence mutation aimed at improving stability may also be employed within the context of the invention.

As mentioned above, the detection method disclosed in PCT Patent Publication WO 2014/114780 and in US Patent Publication No. 2015-0361178 involves the use of a capture moiety capable of binding the VDR-LBD/1,25(OH)$_2$D complex by specifically recognizing the conformationally modified VDR-LBD bound to 1,25(OH)$_2$D or analog thereof, without cross-reacting with uncomplexed VDR-LBD.

Preferably, the antibody of the invention is a monoclonal antibody, and more preferably, the monoclonal antibody disclosed in PCT Patent Publication WO 2014/114780 and in US Patent Publication No. 2015-0361178. As disclosed therein, a number of hybridoma clones producing monoclonal antibodies which are able to specifically recognize and bind to the conformationally modified VDR-LBD bound to 1,25(OH)$_2$D without substantially cross-reacting with uncomplexed VDR-LBD, were produced. Methods for producing such antibodies are disclosed in PCT Patent Publication WO 2014/114780 and in US Patent Publication No. 2015-0361178. In brief, individual use aliquots of the immunogen (i.e., the binding domain of VDR-LBD bound to 1,25(OH)$_2$D), formulated with the appropriate adjuvant are injected into BALB/c mice. Following 4-, 6- and 8-weeks, lymphocytes from mice spleens are fused with SP2/0 mouse myeloma cells using polyethylene glycol (PEG) as fusion agent. The hybrid cells are plated over 384 wells in a high through-put 96 well culture plate format.

The hybridoma clone, designated as 11B4H11H10, was isolated in this manner, and found to produce a monoclonal antibody that was fully characterized by sequencing in order to identify the nucleic acid and amino acid sequences of its heavy and light chain variable domains (see, PCT Patent Publication WO 2014/114780 and US Patent Publication No. 2015-0361178). The CDRs (CDR1, CDR2 and CDR3) of both the heavy and light chain variable domains were also identified.

Such nucleic and amino acid sequences are illustrated in the Sequence Listing, which forms an integral part of the description; in the Sequence Listing, the amino acid and nucleic acid sequences of the heavy chain variable domain of 11B4H11H10 are designated as SEQ ID NO:7 and SEQ ID NO:8, respectively; the amino acid and nucleic acid sequences of the light chain variable domain of 11B4H11H10 are designated as SEQ ID NO:9 and SEQ ID NO:10, respectively; the CDRs of the heavy chain variable domain of 11B4H11H10 are designated as SEQ ID NOs:1, 2 and 3 and the CDRs of the light chain variable domain of 11B4H11H10 are designated as SEQ ID NOs:4, 5 and 6.

Therefore, according to a preferred embodiment, the antibody of the invention is a monoclonal antibody comprising a heavy chain variable domain and a light chain variable domain, wherein the heavy chain variable domain comprises at least one CDR selected from the group consisting of SEQ ID NOs:1, 2 and 3 and/or the light chain variable domain comprises at least one CDR selected from the group consisting of SEQ ID NOs:4, 5 and 6.

In a more preferred embodiment, the heavy chain variable domain comprises one, two or all three of the CDRs SEQ ID NOs:1, 2 and 3 and/or the light chain variable domain comprises one, two or all three of the CDRs SEQ ID NOs:4, 5 and 6.

In a particular embodiment, the heavy chain variable domain comprises the amino acid sequence SEQ ID NO:7 or is encoded by a nucleic acid comprising the sequence SEQ ID NO:8 and/or the light chain variable domain comprises the amino acid sequence SEQ ID NO:9 or is encoded by a nucleic acid comprising the sequence SEQ ID NO:10.

The present study was designed using a new, fully-automated 1,25(OH)$_2$D assay with improved analytical performance, sensitivity, and reliability. The inventors tested the hypothesis that levels of 1,25(OH)$_2$D and its ratio to PTH are biomarkers that allow for risk prediction or stratification of worsening renal function (WRF) in patients at risk of renal injury or in patients affected by renal injury.

As discussed above, prior determinations for Vitamin D sufficiency have relied upon determining levels of circulating 25-Hydroxyvitamin D (25(OH)D) (calcifediol), which is produced in the liver by hydroxylation of vitamin D (cholecalciferol) but which is biologically inactive. 25(OH)D is used for such determinations as bone weakness, bone malformation, or abnormal metabolism of calcium (reflected by abnormal calcium, phosphorus, PTH) occurring as a result of a deficiency or excess of vitamin D. However, circulating 25(OH)D is transported to the kidneys where it is converted to its active form 1,25(OH)$_2$D (calcitriol). 1,25(OH)$_2$D acts on the gastrointestinal tract to promote the absorption of dietary calcium, acts upon the kidney to increase renal tubular reabsorption of calcium, and on the bone to mobilize calcium. 1,25(OH)$_2$D circulates in the blood bound to the vitamin D binding protein, and enters target cells where the 1,25(OH)$_2$D is made available to bind to the vitamin D receptor (VDR). This ligand/receptor complex readily translocates across the nuclear membrane to act as a transcription factor. 1,25(OH)$_2$D is now known to have a broader spectrum of action, and has been associated with increased risks for various chronic infectious and autoimmune conditions, diabetes, cancer, cardiovascular ailments, hypertension, obesity and overweight and complications during pregnancy. Therefore, the inventors hypothesized that 1,25(OH)$_2$D levels may be more indicative of homeostatic health and aberrations therefrom as manifested in cardiac, intestinal, immune, bone, neuronal degenerative, cancerous and diabetic conditions. While serum 1,25(OH)$_2$D values are not generally taken, it is considered that normal circulating levels of 1,25(OH)$_2$D in the United States are in the range of 19.9-79.3 pg/ml with a median of about 47.8 pg/ml (LIAISON® XL 1,25 Dihydroxyvitamin D Assay (REF 310980, REF 310981) IFU (Instructions for Use)).

Since the binding of 1,25(OH)$_2$D to the VDR-LBD is known to induce a conformational change, immunoassay methods for detecting total 1,25(OH)$_2$D may involve the use of a conformation-specific capture moiety, such as an antibody, capable of specifically recognizing and binding to VDR-LBD bound to 1,25(OH)$_2$D, in order to selectively discriminate the VDR-LBD/1,25(OH)$_2$D complex from either unbound 1,25(OH)$_2$D or unbound VDR-LBD, as described in WO 2014/114780. Preferably, the capture moiety of the method of the invention is a monoclonal antibody specific to the VDR-LBD-1,25(OH)$_2$D complex conformation.

Furthermore, in such detection methods, the detection of the captured VDR-LBD/1,25(OH)$_2$D complex may be accomplished through a detectable signal, which is generated directly, for example, by employing a labeled receptor protein or indirectly, for example, via a labeled detector molecule which is capable of specifically binding the VDR-LBD/1,25(OH)$_2$D complex captured by the capture moiety. Typically, the detector molecule is an antibody directed to an epitope on the VDR-LBD/1,25(OH)$_2$D complex which is different from the epitope recognized by the capture moiety.

According to a preferred embodiment, the 1,25(OH)$_2$D immunoassay of the method of the invention is a sandwich immunoassay, more preferably a chemiluminescence immunoassay. Depending on the format of the immunoassay, the capture antibody may be immobilized on or to a solid support. Non-limiting examples of suitable solid supports are the wells of a microtitre plate, the surface of a microparticle such as a latex, polystyrene, silica, chelating sepharose or magnetic beads, membranes, strips or chips.

The antibody of the present invention is preferably produced by animal immunization. Briefly, monoclonal antibodies are generated by injecting animals, for example rats, hamsters, rabbits or mice, with an immunogen comprising the conformationally modified VDR-LBD bound to 1,25-(OH)$_2$ vitamin D or analog thereof, according to methods known per se (Costagliola et al., J Immunol 1998; 160:1458-65). The presence of specific antibody production is monitored after the initial injection and/or after a booster injection by performing an immunodetection assay on a serum sample obtained from the injected animals. From the animals which are found to produce the specific antibody(ies) of interest, spleen cells are removed and subsequently fused with a myeloma cell fusion partner to generate hybridoma cell lines which are then screened for their ability to secrete the antibody(ies) of interest, i.e., antibodies which specifically bind to the VDR-LBD of the complex formed between VDR-LBD and 1,25(OH)$_2$D or analog thereof.

In the detection method of the present invention, the detection of the captured VDR-LBD/1,25(OH)$_2$D complex may be accomplished through a wide range of techniques. For example, a detectable signal may be generated directly by employing a labeled receptor protein or indirectly via a labeled detector molecule which is capable of binding the VDR-LBD/1,25(OH)$_2$D complex captured by the capture moiety. Typically, the detector molecule is another antibody directed to an epitope on the VDR-LBD/1,25(OH)$_2$D complex which is different from the epitope recognized by the capture moiety of the invention (i.e., an anti-VDR-LBD detector antibody).

The detectable label may be any substance capable of producing a signal that is detectable by visual or instrumental means. Suitable labels for use in the present invention include for example fluorescent compounds, chemiluminescent compounds, radioactive compounds, enzymes and enzyme substrates, molecules suitable for colorimetric detection, binding proteins, epitopes, enzymes or substrates. In practice, any signal molecule or label known in the art may be incorporated in embodiments of the method and kit of the present invention.

Any assay format which enables contact between the biological fluid sample and the receptor protein comprising the Ligand Binding Domain of Vitamin D Receptor (VDR-LBD) is suitable for carrying out the detection method of the invention.

According to a preferred embodiment, the detection method of the invention is an in vitro immunoassay performed on a biological fluid sample of a subject or patient. Immunoassays include both homogeneous and heterogeneous assays, as well as competitive and non-competitive sandwich assays.

Figure 2:
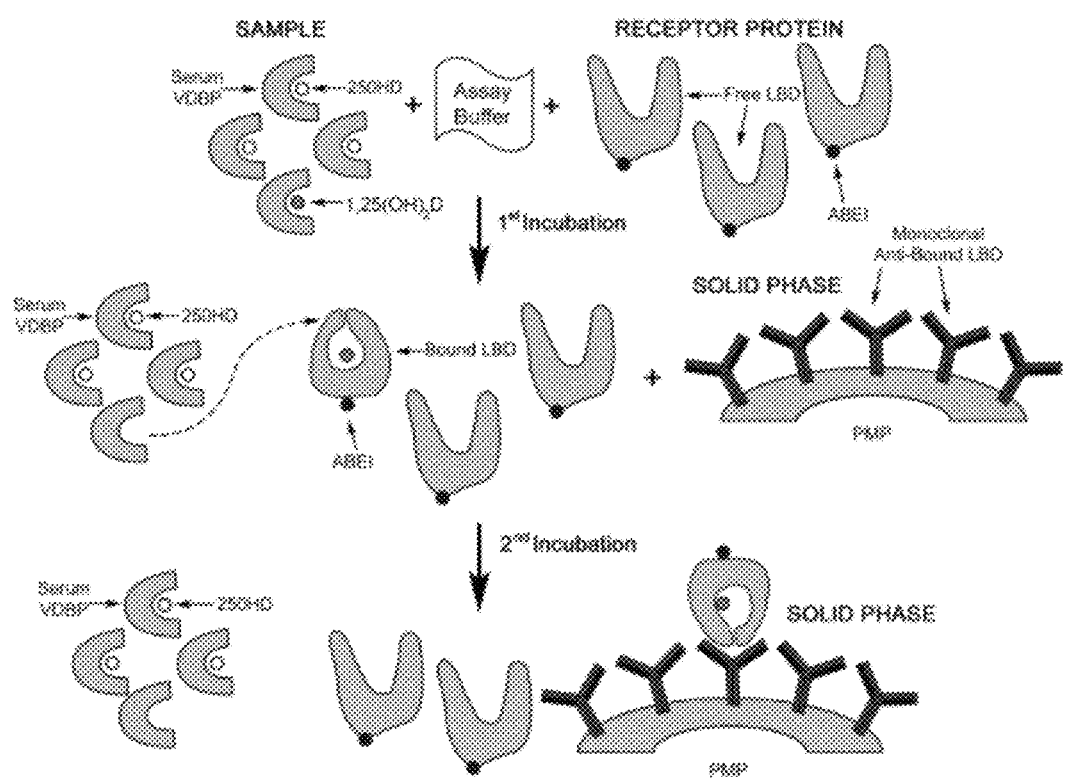
FIG. 2 Illustrates one-site, non-competitive immunoassays according to the invention, wherein the complex formed via the binding of 1,25(OH)$_2$D to the labeled receptor protein which comprises the Ligand Binding Domain of Vitamin D Receptor (VDR-LBD) is captured by the conformation-specific capture antibody of the invention (designated as "Monoclonal Anti-Bound LBD") immobilized on or to a solid support (a paramagnetic particle (PMP)) and the label is Amino-Butyl-Ethyl-Isoluminol (ABEI). The step of adjusting the pH of the biological fluid sample with the assay buffer and the step of adding the receptor protein comprising the VDR-LBD to the sample, are carried our sequentially.

By way of example, one-site, non-competitive immunoassays may be conducted as described in PCT Patent Publication WO 2014/114780 and in US Patent Publication No. 2015-0361178 (FIG. 1 and FIG. 2), wherein the complex formed via the binding of 1,25(OH)$_2$D to the labeled receptor protein which comprises the Ligand Binding Domain of Vitamin D Receptor (VDR-LBD) is captured by the conformation-specific capture antibody of the invention (which in FIG. 1 and FIG. 2 is designated a "Monoclonal Anti-Bound LBD") immobilized on or to a solid support. In the examples of FIG. 1 and FIG. 2, the solid support is a paramagnetic particle (PMP) and the label is Amino-Butyl-Ethyl-Isoluminol (ABEI).

In a specific embodiment described in PCT Patent Publication WO 2014/114780 and in US Patent Publication No. 2015-0361178 (FIG. 1) the step of adjusting the pH of the biological fluid sample with the assay buffer and the step of adding the receptor protein comprising the VDR-LBD to the sample, are performed simultaneously. In the specific embodiment of FIG. 2, such steps are carried out sequentially.

PCT Patent Publication WO 2014/114780 and in US Patent Publication No. 2015-0361178 illustrates (FIG. 3), by way of example, a suitable sandwich immunoassay. The general features and procedures of sandwich immunoassays are well-established and known to the person skilled in the art. A sandwich immunoassay is a particularly preferred embodiment of the method of the present invention.

The sandwich immunoassay disclosed in PCT Patent Publication WO 2014/114780 and in US Patent Publication No. 2015-0361178 (FIG. 3) involves the binding of the VDR-LBD/1,25(OH)$_2$D complex to the conformation-specific capture antibody (designated as "Monoclonal Anti-Bound LBD") immobilized on or to a solid support (e.g. a paramagnetic particle, PMP) and the use of a labeled detector antibody as the second part of the sandwich. The detector antibody is either directly labeled or it is recognized by a conjugate consisting of a labeled anti-immunoglobulin antibody (in the specific example of FIG. 3, the detector antibody is directly labeled with ABEI). The amount of labeled antibody directly or indirectly bound to the VDR-LBD/1,25(OH)$_2$D complex is then measured by suitable means.

A sandwich immunoassay suitable for use in the present invention may involve the use of a tagged receptor protein comprising VDR-LBD in combination with an anti-tag detector antibody. In this embodiment, the detection of the VDR-LBD/1,25(OH)$_2$D complex captured by the conformational-specific capture antibody is achieved by the specific binding of the detector antibody to the tag which is present on the complex. Preferably, the tag is a polyhistidine tag. In a more specific embodiment, the tag is a chaperone protein.

The immunoassays falling within the scope of the invention may, however, be in any suitable format, such as, for example, radioimmunoassays (RIA), chemiluminescence- or fluorescence-immunoassays, Enzyme-linked immunoassays (ELISA), Luminex-based bead arrays, protein microarray assays, or rapid test formats such as, for instance, immunochromatographic strip tests.

Depending on the format of the immunoassay, the capture antibody and/or the detector antibody may be immobilized on or to a solid support. Non-limiting examples of suitable solid supports are the wells of a microtitre plate, the surface of a microparticle such as a latex, polystyrene, silica, chelating sepharose or magnetic beads, membranes, strips or chips.

Parathyroid hormone ("PTH") is secreted by the parathyroid glands and acts to increase the concentration of calcium in the blood by binding to the parathyroid receptor (expressed at high levels in the bone and kidney) or to parathyroid hormone 2 receptor (expressed in the CNS, pancreas, testis and placenta). Further, PTH increases the activity of renal 1-α-hydroxylase, which converts 25-hydroxyvitamin D to 1,25(OH)$_2$D to support endocrine function. 1-α-hydroxylase is also expressed in various other tissues, whose cells may convert 25(OH)D for autocrine and paracrine functions. Normal values for PTH are considered to be 5.72 to 45.4 pg/mL and 5.68 to 47.8 pg/mL in EDTA plasma and serum, respectively (LIAISON® 1-84 PTH Assay (REF 310630, REF 310631) IFU (Instructions for Use). The median for the ratio of 1,25(OH)$_2$D to PTH in normal individuals is approximately 2.7 (range of 1.2-9.1).

The ratio of 1,25(OH)$_2$D to PTH is identified herein as being a biomarker for predicting or stratifying the risk of worsening renal function (WRF) in patients at risk of renal injury or in patients affected by renal injury.

As mentioned above, a further aspect of the present invention is a kit for detecting and quantifying (i.e., determining the amount or concentration) of 1,25(OH)$_2$D or analog thereof in a biological fluid sample, and for additionally detecting PTH in an aliquot of such sample, or in another biological fluid sample of a subject patient. Preferably, the kit will comprise the Vitamin D receptor protein and the capture moiety as defined above in connection with the method, as well as a binding buffer which has a pH comprised between 6 and 9. Preferred pH values are comprised between 7 and 8.6, such as 7.2, 7.3, 7.4, 7.5, 7.6, 7.7, 7.8, 7.9, 8.0, 8.1, 8.2, 8.3, 8.4, 8.5 or 8.6. Preferred but not limiting examples of the binding buffer for adjusting the pH of the test sample include 50 mM Tris buffer (pH 7.4), Hepes (6.5-7.5), PBS. The kit will also contain reagents for detecting and quantifying the amount or concentration of PTH.

The kit of the invention may further comprise a solid support such as, without limitation, beads, microparticles, nanoparticles, super paramagnetic particles, a microtitre plate, a cuvette, a lateral flow device, a flow cell, or any surface to which a protein or peptide can be passively or covalently bound. Either the receptor protein or the capture moiety of the kit of the invention may be immobilized on or to the solid support.

Further, the kit of the invention may contain detection means as described above in connection with the detection method.

Figure 4:
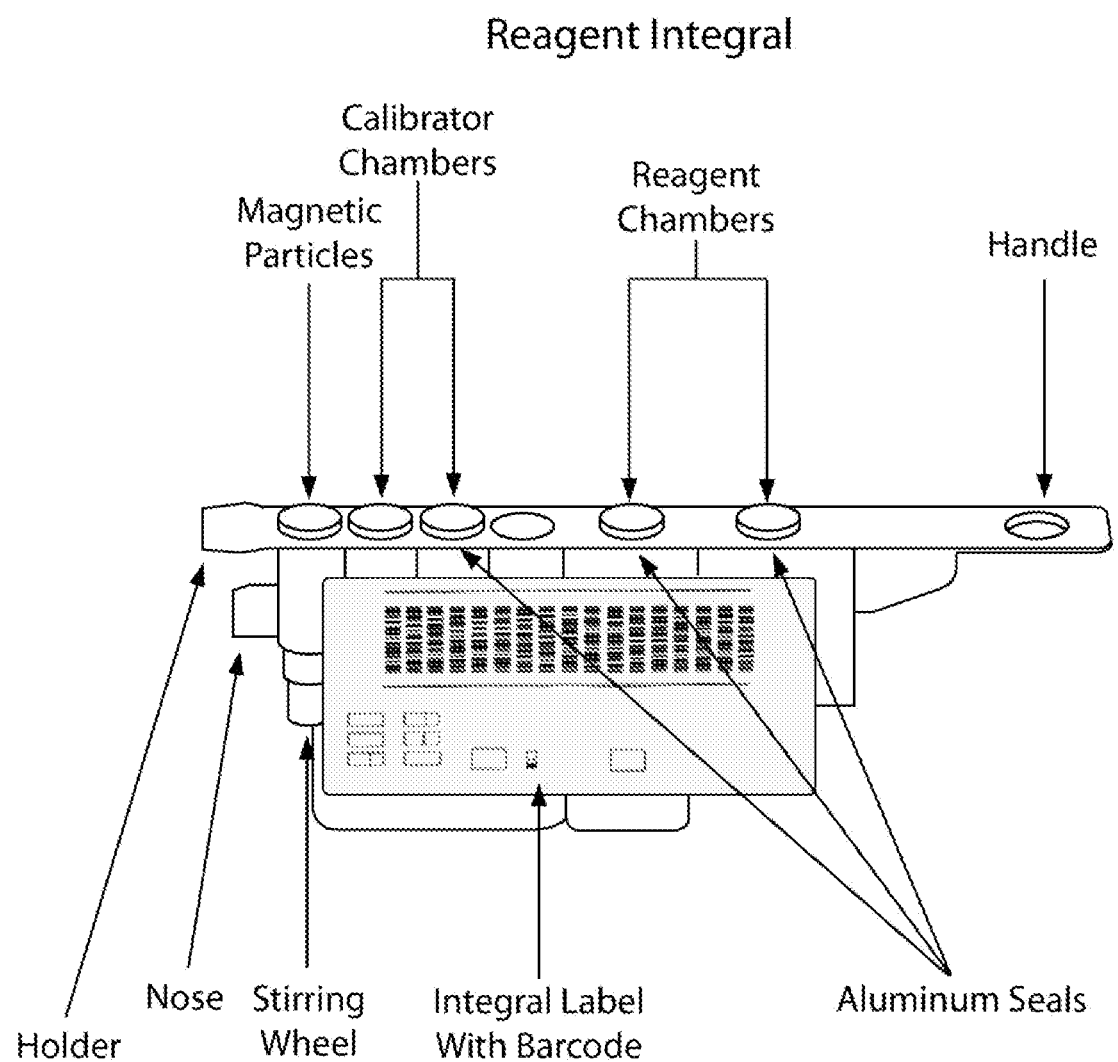
FIG. 4: Illustrates an exemplary Reagent Integral," which is a multi-chambered cartridge that is specially adapted for use in an automated analyzing device, such as the Liaison® Analyzer.

A "Reagent Integral" is a multi-chambered cartridge that is specially adapted for use in an automated analyzing device, such as the Liaison® Analyzer. FIG. 4 shows an exemplary Reagent Integral. A Research Integral will comprise one or more "Reagent Chambers," one or more optional "Calibrator Chambers," which will be sealed to prevent contamination and spillage prior to use, a chamber for mixing reagents, which may have an agitator, such as a stirring wheel. The Research Integral may comprise a handle to facilitate transport, and a nose to facilitate movement of the Research Integral within the analyzer. The respective "Reagent Chambers" hold reagents needed to conduct a desired assay, and are constructed of a non-reactive material (e.g., glass, plastic, resin, etc.). The Reagent Integral is preferably accompanied by software, barcodes, etc. that is used by the automated analyzing device to analyze the obtained data. The Reagent Integrals may additionally comprise one or more "Calibrator Chambers" that are specific to each Research Integral, and that are assayed to create a "Working Curve," in conjunction with the Research Integral's software (which provides a "Master Curve").

In some embodiments, the Research Integral will be specially adapted to analyze a reagent by conducting an assay for that reagent in accordance with a particular assay format, such as a format in which one or more reactants is immobilized on or to a solid support. Preferably, this is accomplished by immobilizing such reagent directly or indirectly to a magnetic bead present in a chamber or container of the Reagent Integral, and thus the Reagent Integral may comprise a chamber or container that contains such beads.

Thus, such Reagent Integral kits are adapted to be used to analyze the concentrations or amounts of one or more target analytes in a biological sample (e.g., serum, plasma, blood, etc.) (and particularly in aliquots of the same biological sample) of a patient. In a preferred embodiment, a kit of the present invention will be a "Reagent Integral" that is specially adapted for determining the concentrations or amounts of 1,25-dihydroxyvitamin D and PTH. In a more preferred embodiment, such a Reagent Integral kit of the present invention is a single multi-chambered cartridge specially adapted for determining the concentrations or amounts of both 1,25-dihydroxyvitamin D and PTH. Thus, in a preferred embodiment, a Reagent Integral kit of the present invention will comprise:

(A) a first container (e.g., a Reagent Chamber) that contains Ligand Binding Domain of Vitamin D Receptor (VDR-LBD) and an antibody, or epitope-binding fragment thereof, that specifically binds to a conformational epitope of VDR-LBD when the VDR-LBD is complexed with 1,25-dihydroxyvitamin D in serum or plasma or blood, and does not specifically bind to VDR-LBD or to 1,25-dihydroxyvitamin D that are not complexed with one another; and (B) a second container (e.g., a Reagent Chamber) that contains a detectably-labelled reagent capable of binding to parathyroid hormone (PTH).

In a preferred embodiment, the antibody, or epitope-binding fragment thereof, that specifically binds to the conformational epitope of VDR-LBD is immobilized on or to a solid support in the first container. In a further embodiment, the antibody, or epitope-binding fragment thereof, of the first container is a monoclonal antibody (or epitope-binding fragment thereof). In a further embodiment, the antibody, or epitope-binding fragment thereof, of the first container may be detectably labeled.

Various exemplary embodiments of devices and compounds as generally described above and methods according to this invention will be understood more readily by reference to the following examples, which are provided by way of illustration and are not intended to be limiting of the invention in any fashion.

EXPERIMENTAL SECTION

Example 1: 1,25(OH)$_2$D Assay

One of the preferred embodiment of the assay of the invention is described in PCT Patent Publication WO 2014/114780 and in US Patent Publication No. 2015-0361178. In brief, paramagnetic microparticles (PMPs) (Dynal, Norway) were coated with a conformation-specific monoclonal antibody capable of recognizing the VDR-LBD/1,25(OH)2D complex antibody following the supplier instructions. The recombinant VDR-LBD that was used in the assay was prepared as described in Example 1, and was coupled to an affinity tag (designated in the following as "TAG"). The 11B4H11H10 monoclonal antibody, described above, was used for this purpose. A mouse monoclonal anti-TAG antibody was conjugated with cyclic AminoButhylEthylisoluminol (cABEI) in PBS buffer pH 7.4. The calculated cABEI incorporation was from 2-3 molecules per antibody molecule. Calibrators were prepared by adding different concentrations of an ethanolic solution of 1,25(OH)$_2$D into a steroid-free, charcoal-stripped human serum. The assay buffer formulation consisted of TRIS 50 mM pH 7.4, CHAPS 0.02%, EDTA 1 mM, heparin at 8 mg/ml and 1% mouse serum to mitigate heterophilic human anti mouse (HAMA) interferences.

A major challenge of an automated assay not using any off-line pre-analytical/sample pre-treatment steps is the ability of the assay to specifically capture and detect the whole amount of 1,25(OH)$_2$D, or analogues of the active form of vitamin D, in a biological matrix (e.g. serum or plasma) without interference by other vitamin D metabolites such as 25(OH)D, 24,25(OH)$_2$D and 25,26(OH)$_2$D which can be present at levels 1000-fold higher than 1,25(OH)$_2$D. This challenge is further complicated by the presence of Vitamin D binding protein (DBP) and albumin, which are abundant in circulation and serve as the major binding proteins for 25(OH)D, 1,25(OH)$_2$D, and other metabolites of vitamin D, whereby 85% to 90% is bound to DBP and 10 to 15% is bound to albumin. Furthermore, DBP levels increases up to 2-5 fold in high-estrogen states, such as pregnancy.

Figure 3:
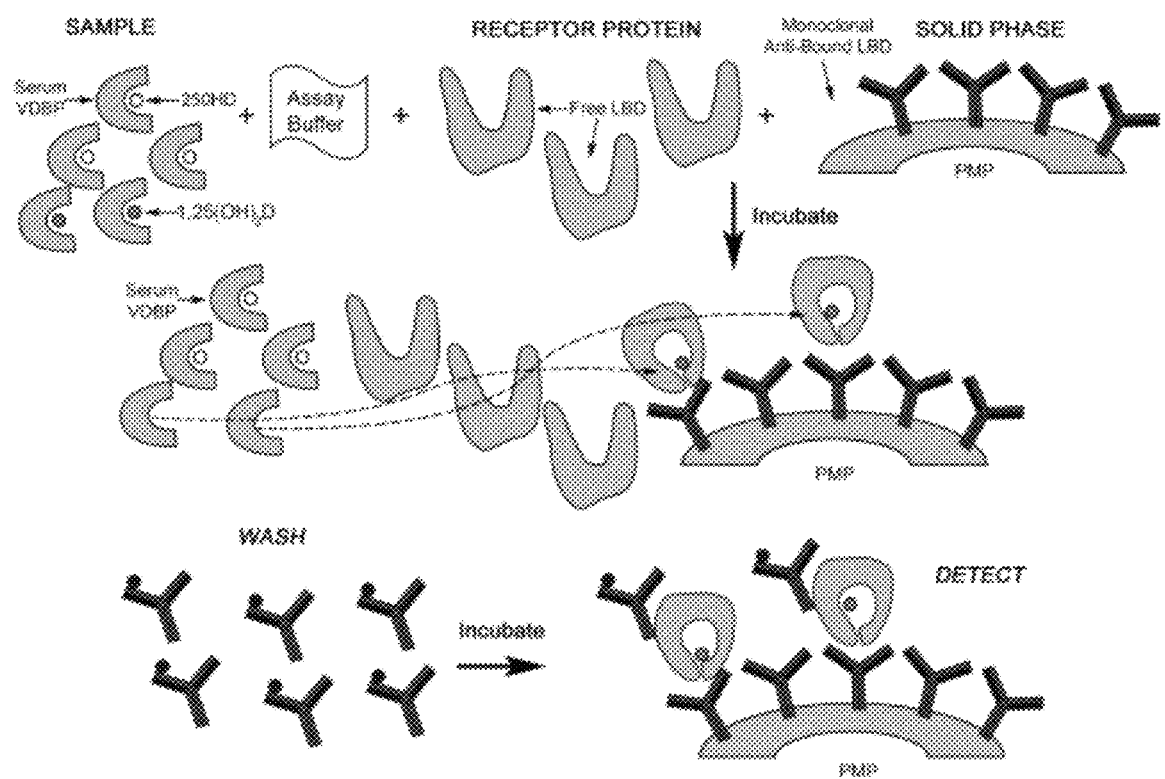
FIG. 3 Illustrates a sandwich immunoassay which involves the binding of the VDR-LBD/1,25(OH)2D complex to the conformation-specific capture antibody (designated as "Monoclonal Anti-Bound LBD") immobilized on or to a solid support (e.g. a paramagnetic particle, PMP) and the use of a labeled detector antibody as the second part of the sandwich. The detector antibody is either directly labeled or it is recognized by a conjugate consisting of a labeled anti-immunoglobulin antibody (in the specific example of FIG. 3 the detector antibody is directly labeled with ABEI). The amount of labeled antibody directly or indirectly bound to the VDR-LBD/1,25(OH)2D complex is then measured by suitable means

The assay schematically illustrated in FIG. 3 was carried out on the DiaSorin LIAISON® analyzer (Saluggia, Italy). First, 50 µl of human serum sample was incubated with 100 µl of assay buffer and 50 µl of VDR-LBD-TAG for 30 minutes. Next, 20 µl of PMPs coated with 11B4H11H10 monoclonal antibody were added and the reaction mixture was incubated for an additional 30 minutes. After washing the reaction mixture, 40 µl of cABEI-conjugated anti TAG monoclonal antibody was added and the reaction mixture incubated for an additional 30 min. After a second wash, trigger solutions were added and the reaction mixture was read as Relative Lights Units (RLUs) in the analyzer reading chamber.

Example 2: The 1,25(OH)$_2$D/PTH Ratio as Biomarker of Renal Injury

Materials and Methods

The cohort studied consisted of 1083 patients enrolled in a biomarker substudy of a randomized, double-blind, placebo controlled, multicenter study that enrolled 6975 patients with clinical evidence of chronic and stable HF (NYHA II-IV), irrespective of the cause and the level of left ventricular ejection fraction (LVEF). In relation to renal function, 180 patients of the cohort were normal (i.e., eGFR (mL/min/1.73 m$^2$)≥90) and the remainder had eGFR below 90. Venous blood samples were drawn on EDTA at randomization and after three months of follow-up. Patients rested supine for at least 15 min before blood sampling. Blood was centrifuged at 4° C. within 10 minutes of draw and plasma aliquots were shipped on dry ice to a central laboratory. Samples were stored at −70° C. until assayed. In the analysis, worsening of renal function (WRF) was employed as the endpoint.

The plasma concentrations of 1,25-dihydroxyvitamin D (1,25(OH)$_2$D) and PTH were assayed in a central laboratory in a blinded fashion and in a single batch. 1,25(OH)$_2$D was determined with a new fully automated and sensitive immunoassay that uses a recombinant fusion construct of the vitamin D receptor ligand binding domain for specific capture of 1,25(OH)$_2$D (DiaSorin, Saluggia, Italy) and a conformation-specific monoclonal antibody capable of recognizing the VDR-LBD/1,25(OH)2D complex antibody, such as the 11B4H11H10 (also referred to as "11B4") monoclonal antibody. The limit of quantitation for this 1,25(OH)$_2$D assay is 5 pg/mL and the reference interval determined in healthy volunteers ranged between 19.9 and 79.3 pg/mL with a median of 47.8 pg/mL. PTH levels were determined using a sensitive immune assay for the determination of PTH in blood, serum or plasma (Liaison 1-84 PTH, DiaSorin, Saluggia, Italy, #310630) with a measurement range of between 4 and 1800 pg/ml, with the limit of detection being 1.7 pg/ml and the limit of quantitation being 4 pg/ml. The reference interval determined for healthy 25(OH)D sufficient, volunteers ranged from 5.5 to 48 (LIAISON® 1-84 PTH Assay (REF 310630, REF 310631) IFU (Instructions for Use)) with a median of 15.3 pg/ml.

Serum creatinine was measured in local laboratories as part of a national quality control surveillance, at randomization and during follow-up after 1, 3, 6, 12, 24, 36, 48 and 60 months. Glomerular filtration rate (eGFR, mL/min/1.73 m$^2$) was estimated using the simplified modification of diet in renal disease (MDRD) formula. WRF was defined as the first increase in serum creatinine concentration ≥0.3 mg/dL and ≥25% at two consecutive measurements at any time during the study (Damman, K. et al. (2014) "*Terminology and Definition of Changes to Renal Function in Heart Failure,*" Eur. Heart J. 35(48):3413-3416).

Statistical Methods:

Continuous variables were expressed as mean±SD if normally distributed or median [Q1-Q3], as appropriate; categorical variables were reported as absolute numbers and percentages.

Linear multilevel analysis was used to assess the association of baseline patient characteristics with decreasing baseline levels of the 1,25(OH)$_2$D to PTH ratio, which was transformed on a natural logarithmic scale. The model allowed consideration of variable patient characteristics as fixed effects whereas multiple clinical centers introduced random effects.

A Cox proportional hazards model aiming to assess the independent prognostic value of the 1,25(OH)$_2$D to PTH ratio on the occurrence of WRF was built, adjusting for the covariates that were statistically significant in the univariate analysis (P<0.05). Similarly, multivariable Cox models were adopted for the secondary outcomes of the present analysis.

For all of the categorical variables, the proportionality of risk required by the Cox model was assessed using Schoenfeld residuals. The ratio was initially fitted as a single continuous measurement. Because there was clear evidence of non-linearity of risk detected by the restricted cubic splines technique (RCS), it was transformed with natural logarithms, hence satisfying the linearity assumption imposed by the Cox model.

To establish the incremental prognostic value of the 1,25(OH)$_2$D to PTH ratio on the occurrence of WRF, in addition to the conventional risk factors that emerged as statistically significant in the multivariable model, the category-free Net Reclassification Index (cfNRI) was calculated (Pencina, M. J. et al. (2011) "*Extensions of Net Reclassification Improvement Calculations to Measure Usefulness of New Biomarkers,*" Stat. Med. 30:11-21).

A 2-sided P value of <0.05 was considered statistically significant. Statistical analyses were performed with SAS software, version 9.3 (SAS Institute, Inc., Cary, N.C.) and with the R program and the rms package (http://CRAN.R-project.org/package=rms).

Results

Study Population—Baseline Characteristics:

The distribution of baseline characteristics and laboratory values across the entire cohort according to 25(OH)D and 1,25(OH)$_2$D levels are displayed in Table 1.

Univariate and Multivariable Cox Proportional Hazard Models

COX proportional hazard (CPH) analyses were carried out by entering biomarker concentration values into the models as log e-transformed variables. Table 2 shows the results of the Cox proportional hazard analysis for the association of WRF with baseline 1,25(OH)2D alone, PTH alone and their ratio. WRF occurred at 189 [82-735] days after randomization (equivalent to 6.2 [2.7-24.1] months) (median [Q1-Q3]).

TABLE 1

| Variable | All N = 1130 | No WRF N = 795 (70.4%) | WRF N = 335 (29.6%) | P |
|---|---|---|---|---|
| Age (years) | 66.8 ± 10.8 | 66.2 ± 11.1 | 68.1 ± 9.8 | 0.004 |
| Sex (% males) | 917 (81.2) | 638 (80.3) | 279 (83.3) | 0.23 |
| BMI (kg/m$^2$) | 26.8 ± 4.3 | 26.7 ± 4.4 | 26.9 ± 4.2 | 0.49 |
| NYHA III-IV (%) | 290 (25.7) | 191 (24.0) | 99 (29.6) | 0.052 |
| Ischemic HF (%) | 579 (51.2) | 400 (50.3) | 179 (53.4) | 0.34 |
| HR (bpm) | 71.5 ± 13.6 | 70.9 ± 13.0 | 72.5 ± 14.7 | 0.07 |
| SBP (mmHg) | 124.9 ± 18.8 | 125.0 ± 18.8 | 125 ± 19.0 | 0.64 |
| DBP (mmHg) | 76.4 ± 10.4 | 76.7 ± 10.4 | 75.7 ± 10.5 | 0.14 |
| LVEF (%) | 33.1 ± 9.4 | 33.4 ± 9.3 | 32.5 ± 9.5 | 0.18 |
| CVP >6 cm H$_2$O (%) | 89 (7.9) | 61 (7.7) | 28 (8.4) | 0.70 |
| Medical History | | | | |
| Previous MI (%) | 495 (43.8) | 338 (42.5) | 157 (46.9) | 0.18 |
| Previous stroke (%) | 53 (4.7) | 36 (4.5) | 17 (5.1) | 0.69 |
| History of hypertension (%) | 619 (54.8) | 427 (53.7) | 192 (57.3) | 0.27 |
| History of diabetes (%) | 295 (26.1) | 201 (25.3) | 94 (28.1) | 0.33 |
| History of atrial fibrillation (%) | 208 (18.4) | 137 (17.2) | 71 (21.2) | 0.12 |
| History of COPD (%) | 210 (18.6) | 138 (17.4) | 72 (21.5) | 0.10 |
| Laboratory parameters | | | | |
| Serum creatinine (mg/dL) | 1.20 ± 0.42 | 1.16 ± 0.37 | 1.29 ± 0.45 | <0.0001 |
| eGFR (mL/min/1.73 m$^2$) | 68.6 ± 23.5 | 71.0 ± 23 | 63.7 ± 22.9 | <0.0001 |
| Serum bilirubin (mg/dL) | 0.84 ± 0.55 | 0.86 ± 0.61 | 0.80 ± 0.36 | 0.07 |
| Serum fibrinogen (mg/dL) | 375 ± 108 | 372 ± 104 | 379 ± 118 | 0.36 |
| Serum cholesterol (mg/dL) | 190 ± 41 | 193 ± 42 | 184 ± 40 | 0.002 |
| Serum LDL-cholesterol (mg/dL) | 115 ± 36 | 118 ± 36 | 111 ± 35 | 0.006 |

TABLE 1-continued

| Variable | All N = 1130 | No WRF N = 795 (70.4%) | WRF N = 335 (29.6%) | P |
|---|---|---|---|---|
| Serum HDL-cholesterol (mg/dL) | 47 ± 15 | 48 ± 15 | 44 ± 15 | 0.0004 |
| Serum triglycerides (mg/dL) | 123 [91-174] | 123 [90-176] | 124 [93-168] | 0.90 |
| Medical Therapy | | | | |
| ACEi (%) | 926 (82.0) | 645 (81.1) | 281 (83.9) | 0.27 |
| ARB (%) | 196 (17.4) | 134 (16.9) | 62 (18.5) | 0.50 |
| Diuretics (%) | 1045 (92.5) | 719 (90.4) | 326 (97.3) | <0.0001 |
| Beta-blockers (%) | 771 (68.2) | 549 (69.1) | 222 (66.3) | 0.36 |
| Spironolactone (%) | 479 (42.4) | 313 (39.4) | 166 (49.6) | 0.002 |
| Digitalis (%) | 387 (34.3) | 262 (33.0) | 125 (37.3) | 0.16 |
| ASA (%) | 569 (50.4) | 421 (53.0) | 148 (44.2) | 0.007 |
| Nitrates (%) | 358 (31.7) | 249 (31.3) | 109 (32.5) | 0.69 |
| Amiodarone (%) | 230 (20.4) | 141 (17.7) | 89 (26.6) | 0.0008 |
| Randomization to n-3 PUFA (%) | 569 (50.4) | 407 (51.2) | 162 (48.4) | 0.38 |
| Randomization to rosuvastatin (%) | 334 (50.7) | 235 (50.5) | 99 (51.0) | 0.91 |
| Biomarkers | | | | |
| 1,25(OH)$_2$ vitamin D (pg/mL) | 31.3 [23.0-42.2] | 32.2 [24.1-43.1] | 28.7 [21.4-38.6] | 0.0001 |
| PTH (1-84) (pg/mL) | 33.7 [24.3-49.3] | 32.5 [23.6-46.4] | 36.3 [26.2-53.4] | 0.0008 |
| 1,25(OH)$_2$ vitamin D/PTH | 0.89 [0.55-1.45] | 0.98 [0.60-1.53] | 0.73 [0.46-1.26] | <0.0001 |
| Blood samples drawn in winter (No., %) | 328 (29.0) | 235 (29.6) | 93 (27.8) | 0.26 |

TABLE 2A

| | Univariate | | |
|---|---|---|---|
| | No. | HR [95% CI] | P |
| 1,25(OH)$_2$D | 1098 | 0.61 [0.49-0.75] | <0.0001 |
| PTH (1-84) | 1099 | 1.57 [1.28-1.93] | <0.0001 |
| 1,25(OH)$_2$D/PTH | 1067 | 0.60 [0.52-0.70] | <0.0001 |

When multivariable COX analyses were performed, the following variables were entered into the Cox multivariate models: 1,25(OH)$_2$D/PTH (log e-transformed), age, eGFR (MDRD equation), NYHA class, serum concentrations of total cholesterol and bilirubin, prescriptions of diuretics, spironolactone, aspirin or amiodarone.

TABLE 2B

| | Multivariate | | |
|---|---|---|---|
| | No. | HR [95% CI] | P |
| 1,25(OH)$_2$D | 1043 | 0.76 [0.59-0.97] | 0.03 |
| PTH (1-84) | 1040 | 1.20 [0.95-1.50] | 0.12 |
| 1,25(OH)$_2$D/PTH | 1012 | 0.75 [0.62-0.90] | 0.003 |

Variables significantly associated with WRF in the multivariable models:

With 1,25(OH)$_2$D: serum cholesterol (p=0.0003), amiodarone (p=0.0005), aspirin (p=0.01), diuretics (p=0.02), serum bilirubin (p=0.02), spironolactone (p=0.04).

With PTH: amiodarone (p=0.0003), serum cholesterol (p=0.0004), aspirin (p=0.02), diuretics (p=0.03), spironolactone (p=0.03), serum bilirubin (p=0.04).

With 1,25(OH)$_2$D/PTH: serum cholesterol (p=0.0001), amiodarone (p=0.0008), aspirin (p=0.01), diuretics (p=0.02), spironolactone (p=0.03), serum bilirubin (p=0.04), eGFR (0.05).

Prognostic Accuracy of Baseline 1,25(OH)$_2$D/PTH for WRF

ROC Curves a) ROC Curves of Baseline 1,25(OH)$_2$D/PTH with WRF.

Figure 5:
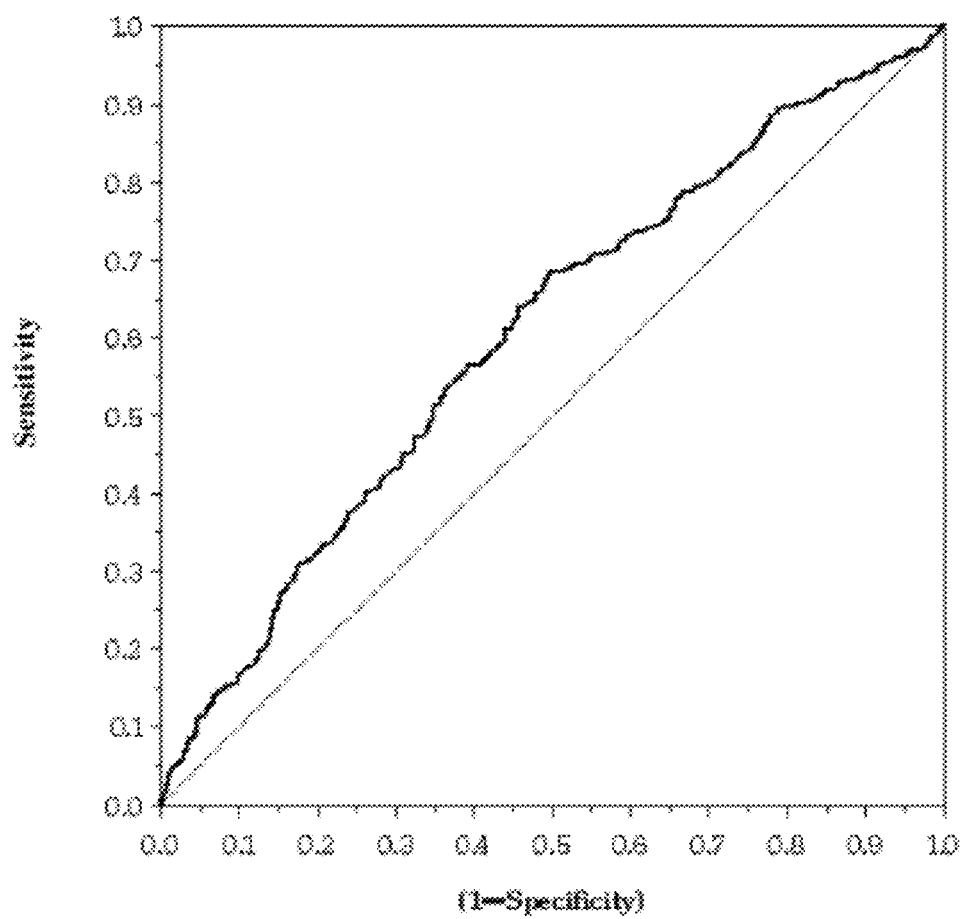
FIG. 5: Receiver operator curve (ROC) and area under the curve (AUC) for the 1,25(OH)$_2$D/PTH ratio with WRF

In ROC analysis, the area under the curve (AUC) criterion was applied to WRF at the end of the 3.9 year follow-up (FIG. 5). The receiver operator curve depicted in FIG. 5 for WRF at 3.9 years follow up to baseline randomization discloses an AUC of 60%, with specificity of 54% and sensitivity of 64% using the optimal 1,25(OH)$_2$D/1-84 PTH ratio threshold of 0.92.

TABLE 3

| | AUROC ± SD | p | Specificity | Sensitivity | Optimal cut-off |
|---|---|---|---|---|---|
| 1,25(OH)$_2$D/PTH | 0.60 ± 0.02 | <0.0001 | 0.54 | 0.64 | 0.92 |

Figure 6:
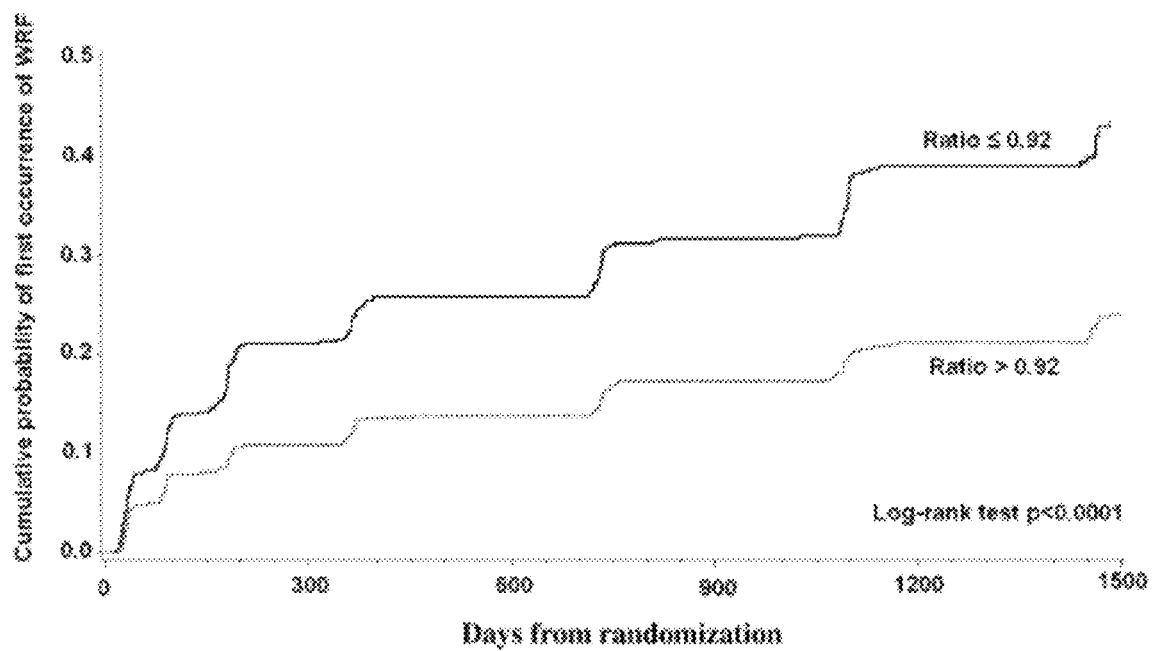
FIG. 6: Kaplan-Meier curve for the first occurrence of WRF stratified by the [1,25(OH)$_2$D]/[PTH] ratio

Kaplan-Meier curves for the first occurrence of WRF according to the 1,25(OH)$_2$D to PTH ratio are presented in FIG. 6. The Kaplan Meier curves in FIG. 6 depict the ability of the 1,25(OH)2D/1-84PTH ratio to discriminate amongst HF subjects those which have a significantly greater likelihood to both develop WRF and whose WRF will progress more quickly. With advancing time post randomization, those HF subjects whose baseline 1,25(OH)2D/1-84PTH ratio were below the 0.92 threshold developed WRF at a faster rate than those whose ratio were >0.92.

b) Maximal Negative Predictive Value

The maximal negative predictive value (NPV=0.82) is observed at a ratio of 1,25(OH)$_2$D to PTH of 1.68, with a sensitivity of 0.90, a specificity of 0.21 and a positive predictive value PPV=0.32. A total of 187 patients (17.5%) have a ratio above the level of 1.68. At this cut-off, the contingency table for the occurrence of WRF is as follows:

|  | WRF | |
|---|---|---|
| N | Yes (positive) | No (negative) |
| 1,25(OH)₂ D/PTH <1.68 (positive) | 285 | 595 |
| ≥1.68 (negative) | 33 | 154 |

True positive: 285/1067=26.7%

False positive: 595/1067=55.8%

False negative: 33/1067=3.1%

True negative: 154/1067=14.4%

Test performance at the cutoff of the ratio 1.68 (maximal NPV):

$$PPV=TP/(TP+FP)=A/(A+B)=285/(285+595)=0.3239$$

$$NPV=TN/(TN+FN)=D/(D+C)=154/(154+33)=0.8235$$

$$Sensitivity=TP/(TP+FN)=A/(A+C)=285/(285+33)=0.8962$$

$$Specificity=TN/(TN+FP)=D/(D+B)=154/(154+595)=0.2056$$

| Statistic | Value (%) |
|---|---|
| Sensitivity | 89.6 |
| Specificity | 20.6 |
| Negative Predictive Value (NPV) | 82.4 |
| Positive Predictive Value (PPV) | 32.4 | c) Best Cut-Off Value

A CART approach was then used to define the best cut-off value of the 1,25(OH)₂D to PTH ratio to predict WRF.

Classification and regression trees (CART) is a model-free approach used to find the best splitting criterion. This method, a form of recursive partitioning, developed on 0.9 of the data allows to validate best on the remaining 0.1 of the data.

At the optimal cut-off of 0.98, the contingency table for the occurrence of WRF is as follows:

|  | WRF | |
|---|---|---|
| N | Yes (positive) | No (negative) |
| 1,25(OH)₂ D/PTH <0.98 (positive) | 217 | 372 |
| ≥0.98 (negative) | 101 | 377 |

True positive: 217/1067=20.3%

False positive: 372/1067=34.9%

False negative: 101/1067=9.5%

True negative: 377/1067=35.3%

Test performance at the cutoff of the ratio >0.98 (best cut-off identified with CART method)

$$PPV=TP/(TP+FP)=A/(A+B)=217/(217+372)=0.3684$$

$$NPV=TN/(TN+FN)=D/(D+C)=377/(377+101)=0.7887$$

$$Sensitivity=TP/(TP+FN)=A/(A+C)=217/(217+101)=0.6823$$

$$Specificity=TN/(TN+FP)=D/(D+B)=377/(377+372)=0.5033$$

| Statistic | Value (%) |
|---|---|
| Sensitivity | 68.2 |
| Specificity | 50.3 |
| Negative Predictive Value (NPV) | 78.9 |
| Positive Predictive Value (PPV) | 36.8 |

While this invention has been described in conjunction with the various exemplary embodiments outlined above, various alternatives, modifications, variations, improvements and/or substantial equivalents, whether known or that are or may be presently unforeseen, may become apparent to those having at least ordinary skill in the art. Accordingly, the exemplary embodiments according to this invention, as set forth above, are intended to be illustrative not limiting. Various changes may be made without departing from the spirit and scope of the invention. Therefore, the invention is intended to embrace all known or later-developed alternatives, modifications, variations, improvements and/or substantial equivalents of these exemplary embodiments.

DISCUSSION

The present inventors found that the ratio of circulating 1,25(OH)₂D and PTH, two hormones involved in bone-mineral metabolism, can surprisingly predict deterioration of renal function better than either marker alone. These results were obtained in a large, representative cohort of patients with HF, some of which were affected by renal injury, enrolled in a controlled, multicenter clinical trial.

Early prediction and identification of patients at risk for WRF may be useful to optimize therapies, and to improve outcomes. The search for new markers of changes in renal function is currently very active. They should be more sensitive and specific to early changes in renal function than serum creatinine, which is slowly affected and can be confounded by muscle mass and anthropometric factors.

In the present study, the inventors showed that a low circulating ratio of 1,25(OH)₂D to PTH predicted future episodes of WRF in patients. Although this ratio was strongly associated with concomitant serum creatinine levels, its prognostic value was independent of eGFR estimated from creatinine levels, suggesting a net contribution of vitamin D metabolism to the prediction of WRF.

In conclusion, the ratio of 1,25(OH)₂D to PTH is a new, powerful indicator of future risk of deterioration of renal function in patients at risk of renal injury and affected by renal injury.

What is claimed is:

1. A kit, being an article of manufacture, that comprises:
   (A) a first container that contains:
   (1) a Ligand Binding Domain of Vitamin D Receptor composed of residues 116-423 of the Ligand Binding Domain of Vitamin D Receptor from *Rattus norvegicus* with deletion of a 47 amino acid internal loop (165-211) (rVDR-LBD); and
   (2) a monoclonal antibody, or epitope-binding fragment thereof, that specifically binds to a conformational epitope of rVDR-LBD when said rVDR-LBD is complexed with 1,25-dihydroxyvitamin D in serum or plasma or blood, and does not specifically bind to VDR-LBD or to 1,25-dihydroxyvitamin D that are not complexed with one another, wherein said monoclonal antibody, or said epitope-binding fragment thereof, comprise Heavy Chain CDR1, CDR2 and CDR3 Domains having, respectively, the sequences of SEQ ID NOs:1, 2 and 3, and Light Chain CDR1, CDR2 and CDR3 Domains having, respectively, the sequences of SEQ ID NOs:4, 5 and 6; and
   (B) a second container that contains a detectably-labeled reagent capable of binding to parathyroid hormone (PTH).

2. The kit according to claim 1, wherein said monoclonal antibody, or epitope-binding fragment thereof, that specifically binds to said conformational epitope of rVDR-LBD is immobilized to a solid support in said first container.

3. The kit according to claim 2, wherein said solid support is a magnetic or paramagnetic bead.

4. The kit according to claim 1, wherein said rVDR-LBD is detectably labeled with a fluorescent label, a chemiluminescent label, a radioactive label, an enzyme label, or a colorimetric label.

5. The kit according to claim 1, wherein said monoclonal antibody, or said epitope-binding fragment thereof comprises a heavy chain variable domain that comprises the sequence of SEQ ID NO:7 and a light chain variable domain that comprises the sequence of SEQ ID NO:9.

6. The kit according to claim 1, wherein said kit is a Reagent Integral that is a multi-chambered cartridge specially adapted for use in an automated analyzing device, wherein said first and second containers of said kit are Reagent Chambers of said Reagent Integral.

7. The kit according to claim 6, wherein said monoclonal antibody, or said epitope-binding fragment thereof, of said Reagent Integral that specifically binds to said conformational epitope of rVDR-LBD is immobilized to a solid support in said first container.

8. The kit according to claim 7, wherein said solid support is a magnetic or paramagnetic bead.

9. The kit according to claim 6, wherein said rVDR-LBD of said Reagent Integral is detectably labeled with a fluorescent label, a chemiluminescent label, a radioactive label, an enzyme label, or a colorimetric label.

10. The kit according to claim 6, wherein said Reagent Integral additionally comprises one or more Calibrator Chambers.

11. The kit according to claim 6, wherein said monoclonal antibody, or said epitope-binding fragment thereof comprises a heavy chain variable domain that comprises the sequence of SEQ ID NO:7 and a light chain variable domain that comprises the sequence of SEQ ID NO:9.

* * * * *

SEQUENCE LISTING

```
<160> NUMBER OF SEQ ID NOS: 10

<210> SEQ ID NO 1
<211> LENGTH: 10
<212> TYPE: PRT
<213> ORGANISM: Mus musculus

<400> SEQUENCE: 1

Gly Phe Thr Phe Ser Asn Phe Gly Met Gln
1               5                   10

<210> SEQ ID NO 2
<211> LENGTH: 10
<212> TYPE: PRT
<213> ORGANISM: Mus musculus

<400> SEQUENCE: 2

Tyr Ile Ser Ser Gly Ser Ser Thr Ile Tyr
1               5                   10

<210> SEQ ID NO 3
<211> LENGTH: 9
<212> TYPE: PRT
<213> ORGANISM: Mus musculus

<400> SEQUENCE: 3

Ser Gly Leu Ile Asp Gly Phe Ala Tyr
1               5

<210> SEQ ID NO 4
<211> LENGTH: 11
<212> TYPE: PRT
<213> ORGANISM: Mus musculus

<400> SEQUENCE: 4

His Ala Ser Gln Gly Ile Ser Ser Asn Ile Gly
1               5                   10

<210> SEQ ID NO 5
<211> LENGTH: 7
<212> TYPE: PRT
<213> ORGANISM: Mus musculus

<400> SEQUENCE: 5

His Gly Thr Asn Leu Glu Asp
1               5

<210> SEQ ID NO 6
<211> LENGTH: 9
<212> TYPE: PRT
<213> ORGANISM: Mus musculus

<400> SEQUENCE: 6

Val Gln Tyr Ala Gln Phe Pro Phe Thr
1               5

<210> SEQ ID NO 7
<211> LENGTH: 110
<212> TYPE: PRT
<213> ORGANISM: Mus musculus

<400> SEQUENCE: 7

Gly Gly Leu Val Gln Pro Gly Gly Ser Arg Lys Leu Ser Cys Ala Ala
1               5                   10                  15
```

Ser Gly Phe Thr Phe Ser Asn Phe Gly Met Gln Trp Val Arg Ala
            20                  25                  30

Pro Glu Lys Gly Leu Glu Trp Val Ala Tyr Ile Ser Ser Gly Ser Ser
        35                  40                  45

Thr Ile Tyr Tyr Ala Asp Thr Val Lys Gly Arg Phe Thr Ile Ser Arg
    50                  55                  60

Asp Asn Pro Lys Asn Thr Leu Phe Leu Gln Met Thr Ser Leu Arg Ser
65                  70                  75                  80

Glu Asp Thr Ala Met Tyr Tyr Cys Ala Arg Ser Gly Leu Ile Asp Gly
                85                  90                  95

Phe Ala Tyr Trp Gly Gln Gly Thr Thr Val Thr Val Ser Ser
            100                 105                 110

<210> SEQ ID NO 8
<211> LENGTH: 330
<212> TYPE: DNA
<213> ORGANISM: Mus musculus

<400> SEQUENCE: 8
ggaggcttag tgcagcctgg agggtcccgg aaactctcct gtgcagcctc tggattcact     60
ttcagtaact ttggaatgca gtgggttcgt caggctccag agaagggct agagtgggtc     120 gcatacatca gtagtggcag tagtaccatc tactatgcag acacagtgaa gggccgattc    180
accatatcca gagacaatcc caagaatacc ctgttcctgc aaatgaccag tctaaggtct    240
gaggacacgg ccatgtatta ctgtgcaaga tcgggtttaa tcgacgggtt tgcttactgg    300
ggccaaggga ccacggtcac cgtctcctca                                     330

<210> SEQ ID NO 9
<211> LENGTH: 95
<212> TYPE: PRT
<213> ORGANISM: Mus musculus

<400> SEQUENCE: 9

Gln Ser Pro Ser Ser Met Ser Val Ser Leu Gly Asp Thr Val Ser Ile
1               5                   10                  15

Thr Cys His Ala Ser Gln Gly Ile Ser Ser Asn Ile Gly Trp Leu Gln
            20                  25                  30

Gln Lys Pro Gly Lys Ser Phe Lys Gly Leu Ile Tyr His Gly Thr Asn
        35                  40                  45

Leu Glu Asp Gly Val Pro Ser Arg Phe Ser Gly Ser Gly Ser Gly Ala
    50                  55                  60

Asp Tyr Ser Leu Thr Ile Ser Ser Leu Glu Ser Glu Asp Phe Ala Asp
65                  70                  75                  80

Tyr Tyr Cys Val Gln Tyr Ala Gln Phe Pro Phe Thr Phe Gly Ser
                85                  90                  95

<210> SEQ ID NO 10
<211> LENGTH: 287
<212> TYPE: DNA
<213> ORGANISM: Mus musculus

<400> SEQUENCE: 10
cagtctccat cctccatgtc tgtatctctg ggagacacag tcagcatcac ttgccatgca     60
agtcagggca ttagcagtaa tataggqtgg ttgcagcaga accagggaa atcatttaag     120

-continued

```
ggcctgatct atcatggaac caacttggaa gatggagttc catcaaggtt cagtggcagt    180
ggatctggag cagattattc tctcaccatc agcagcctgg aatctgaaga ttttgcagac    240
tattactgtg tacagtatgc tcagtttcca ttcacgttcg gctcggg                 287
```